(12) United States Patent
Locke et al.

(10) Patent No.: US 10,406,266 B2
(45) Date of Patent: Sep. 10, 2019

(54) FLUID STORAGE DEVICES, SYSTEMS, AND METHODS

(71) Applicant: KCI Licensing, Inc., San Antonio, TX (US)

(72) Inventors: Christopher Brian Locke, Bournemouth (GB); Timothy Mark Robinson, Shillingstone (GB)

(73) Assignee: KCI LICENSING, INC., San Antonio, TX (US)

( * ) Notice: Subject to any disclaimer, the term of this patent is extended or adjusted under 35 U.S.C. 154(b) by 106 days.

(21) Appl. No.: 15/307,472

(22) PCT Filed: May 4, 2015

(86) PCT No.: PCT/US2015/029037
§ 371 (c)(1),
(2) Date: Oct. 28, 2016

(87) PCT Pub. No.: WO2015/168681
PCT Pub. Date: Nov. 5, 2015

(65) Prior Publication Data
US 2017/0043070 A1 Feb. 16, 2017

Related U.S. Application Data

(60) Provisional application No. 61/988,076, filed on May 2, 2014.

(51) Int. Cl.
*A61F 13/02* (2006.01)
*A61M 1/00* (2006.01)
*A61F 13/00* (2006.01)

(52) U.S. Cl.
CPC ..... *A61M 1/0088* (2013.01); *A61F 13/00068* (2013.01); *A61F 13/0216* (2013.01); *A61M 1/0003* (2013.01)

(58) Field of Classification Search
CPC ............ A61F 13/00068; A61F 13/0216; A61F 13/0213; A61F 13/0203; A61F 13/022
See application file for complete search history.

(56) References Cited

U.S. PATENT DOCUMENTS 1,355,846 A  10/1920 Rannells
1,944,834 A   1/1934 Bennett
(Continued)

FOREIGN PATENT DOCUMENTS

AU   550575 B2   3/1986
AU   745271 B2   3/2002
(Continued)

OTHER PUBLICATIONS

Extended European Search Report for related application 17177013.4, dated Mar. 19, 2018.
(Continued)

*Primary Examiner* — Susan S Su

(57) ABSTRACT

A system suitable for treating a tissue site may include an interface manifold, an interface sealing member, an absorbent layer, and a storage sealing member. The interface manifold may be positioned in fluid communication at the tissue site. The interface sealing member may be adapted to provide a sealed treatment space relative to the tissue site, and the interface manifold may be positioned in the sealed treatment space. The absorbent layer may be for positioning on an exterior facing side of the interface sealing member. The storage sealing member may be adapted to provide a sealed storage space between the storage sealing member and the exterior facing side of the interface sealing member. The absorbent layer may be positioned in the sealed storage space. Other systems, apparatuses, and methods are disclosed.

35 Claims, 7 Drawing Sheets

(56) References Cited

U.S. PATENT DOCUMENTS

| | | |
|---|---|---|
| 2,547,758 A | 4/1951 | Kelling |
| 2,552,664 A | 5/1951 | Burdine |
| 2,632,443 A | 3/1953 | Lesher |
| 2,682,873 A | 7/1954 | Evans et al. |
| 2,860,081 A | 11/1958 | Eiken |
| 2,910,763 A | 11/1959 | Lauterbach |
| 2,969,057 A | 1/1961 | Simmons |
| 3,066,672 A | 12/1962 | Crosby, Jr. et al. |
| 3,172,808 A | 3/1965 | Baumann et al. |
| 3,183,116 A | 5/1965 | Schaar |
| 3,367,332 A | 2/1968 | Groves |
| 3,376,868 A | 4/1968 | Mondiadis |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,742,952 A | 7/1973 | Magers et al. |
| 3,774,611 A | 11/1973 | Tussey et al. |
| 3,777,016 A | 12/1973 | Gilbert |
| 3,779,243 A | 12/1973 | Tussey et al. |
| 3,826,254 A | 7/1974 | Mellor |
| 3,852,823 A | 12/1974 | Jones |
| 3,903,882 A | 9/1975 | Augurt |
| 3,967,624 A | 7/1976 | Milnamow |
| 3,983,297 A | 9/1976 | Ono et al. |
| 4,060,081 A | 11/1977 | Yannas et al. |
| 4,080,970 A | 3/1978 | Miller |
| 4,096,853 A | 6/1978 | Weigand |
| 4,139,004 A | 2/1979 | Gonzalez, Jr. |
| 4,141,361 A | 2/1979 | Snyder |
| 4,163,822 A | 8/1979 | Walter |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,360,015 A | 11/1982 | Mayer |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,414,970 A | 11/1983 | Berry |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,529,402 A | 7/1985 | Weilbacher et al. |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,600,146 A | 7/1986 | Ohno |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,652 A | 5/1987 | Weilbacher |
| 4,664,662 A | 5/1987 | Webster |
| 4,710,165 A | 12/1987 | McNeil et al. |
| 4,715,857 A | 12/1987 | Juhasz et al. |
| 4,733,659 A | 3/1988 | Edenbaum et al. |
| 4,743,232 A | 5/1988 | Kruger |
| 4,753,230 A | 6/1988 | Carus et al. |
| 4,758,220 A | 7/1988 | Sundblom et al. |
| 4,787,888 A | 11/1988 | Fox |
| 4,826,494 A | 5/1989 | Richmond et al. |
| 4,832,008 A | 5/1989 | Gilman |
| 4,838,883 A | 6/1989 | Matsuura |
| 4,840,187 A | 6/1989 | Brazier |
| 4,848,364 A | 7/1989 | Bosman |
| 4,863,449 A | 9/1989 | Therriault et al. |
| 4,871,611 A | 10/1989 | LeBel |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,930,997 A | 6/1990 | Bennett |
| 4,941,882 A | 7/1990 | Ward et al. |
| 4,953,565 A | 9/1990 | Tachibana et al. |
| 4,961,493 A | 10/1990 | Kaihatsu |
| 4,969,880 A | 11/1990 | Zamierowski |
| 4,981,474 A | 1/1991 | Bopp et al. |
| 4,985,019 A | 1/1991 | Michelson |
| 4,995,382 A | 2/1991 | Lang et al. |
| 4,996,128 A | 2/1991 | Aldecoa et al. |
| 5,010,883 A | 4/1991 | Rawlings et al. |
| 5,018,515 A | 5/1991 | Gilman |
| 5,025,783 A | 6/1991 | Lamb |
| 5,028,597 A | 7/1991 | Kodama et al. |
| 5,037,397 A | 8/1991 | Kalt et al. |
| 5,086,170 A | 2/1992 | Luheshi et al. |
| 5,092,323 A | 3/1992 | Riedel et al. |
| 5,092,858 A | 3/1992 | Benson et al. |
| 5,100,396 A | 3/1992 | Zamierowski |
| 5,112,323 A | 5/1992 | Winkler et al. |
| 5,134,994 A | 8/1992 | Say |
| 5,149,331 A | 9/1992 | Ferdman et al. |
| 5,151,314 A | 9/1992 | Brown |
| 5,152,757 A | 10/1992 | Eriksson |
| 5,167,613 A | 12/1992 | Karami et al. |
| 5,176,663 A | 1/1993 | Svedman et al. |
| 5,180,375 A | 1/1993 | Feibus |
| 5,215,522 A | 6/1993 | Page et al. |
| 5,232,453 A | 8/1993 | Plass et al. |
| 5,246,775 A | 9/1993 | Loscuito |
| 5,261,893 A | 11/1993 | Zamierowski |
| 5,266,372 A | 11/1993 | Arakawa et al. |
| 5,270,358 A | 12/1993 | Asmus |
| 5,278,100 A | 1/1994 | Doan et al. |
| 5,279,550 A | 1/1994 | Habib et al. |
| 5,298,015 A | 3/1994 | Komatsuzaki et al. |
| 5,342,329 A | 8/1994 | Croquevielle |
| 5,342,376 A | 8/1994 | Ruff |
| 5,344,415 A | 9/1994 | DeBusk et al. |
| 5,356,386 A | 10/1994 | Goldberg et al. |
| 5,358,494 A | 10/1994 | Svedman |
| 5,384,174 A | 1/1995 | Ward et al. |
| 5,387,207 A | 2/1995 | Dyer et al. |
| 5,419,769 A | 5/1995 | Devlin et al. |
| 5,423,778 A | 6/1995 | Eriksson et al. |
| 5,429,590 A | 7/1995 | Saito et al. |
| 5,437,622 A | 8/1995 | Carion |
| 5,437,651 A | 8/1995 | Todd et al. |
| 5,445,604 A | 8/1995 | Lang |
| 5,447,492 A | 9/1995 | Cartmell et al. |
| 5,458,938 A | 10/1995 | Nygard et al. |
| 5,501,212 A | 3/1996 | Psaros |
| 5,522,808 A | 6/1996 | Skalla |
| 5,527,293 A | 6/1996 | Zamierowski |
| 5,549,584 A | 8/1996 | Gross |
| 5,549,585 A | 8/1996 | Maher et al. |
| 5,556,375 A | 9/1996 | Ewall |
| 5,585,178 A | 12/1996 | Calhoun et al. |
| 5,599,292 A | 2/1997 | Yoon |
| 5,607,388 A | 3/1997 | Ewall |
| 5,611,373 A | 3/1997 | Ashcraft |
| 5,634,893 A | 6/1997 | Rishton |
| 5,636,643 A | 6/1997 | Argenta et al. |
| 5,641,506 A | 6/1997 | Talke et al. |
| 5,645,081 A | 7/1997 | Argenta et al. |
| 5,653,224 A | 8/1997 | Johnson |
| 5,678,564 A | 10/1997 | Lawrence et al. |
| 5,710,233 A | 1/1998 | Meckel et al. |
| 5,714,225 A | 2/1998 | Hansen et al. |

(56) References Cited

U.S. PATENT DOCUMENTS

| | | |
|---|---|---|
| 5,736,470 A | 4/1998 | Schneberger et al. |
| 5,759,570 A * | 6/1998 | Arnold ............... A61F 13/0203 |
| | | 424/443 |
| 5,776,119 A | 7/1998 | Bilbo et al. |
| 5,807,295 A | 9/1998 | Hutcheon et al. |
| 5,878,971 A | 3/1999 | Minnema |
| 5,902,439 A | 5/1999 | Pike et al. |
| 5,919,476 A | 7/1999 | Fischer et al. |
| 5,941,863 A | 8/1999 | Guidotti et al. |
| 5,964,252 A | 10/1999 | Simmons et al. |
| 5,981,822 A | 11/1999 | Addison |
| 5,998,561 A | 12/1999 | Jada |
| 6,071,267 A | 6/2000 | Zamierowski |
| 6,086,995 A | 7/2000 | Smith |
| 6,135,116 A | 10/2000 | Vogel et al. |
| 6,174,306 B1 | 1/2001 | Fleischmann |
| 6,191,335 B1 | 2/2001 | Robinson |
| 6,238,762 B1 | 5/2001 | Friedland et al. |
| 6,241,747 B1 | 6/2001 | Ruff |
| 6,262,329 B1 | 7/2001 | Brunsveld et al. |
| 6,287,316 B1 | 9/2001 | Agarwal et al. |
| 6,345,623 B1 | 2/2002 | Heaton et al. |
| 6,458,109 B1 | 10/2002 | Henley et al. |
| 6,488,643 B1 | 12/2002 | Tumey et al. |
| 6,493,568 B1 | 12/2002 | Bell et al. |
| 6,495,229 B1 | 12/2002 | Carte et al. |
| 6,503,855 B1 | 1/2003 | Menzies et al. |
| 6,548,727 B1 | 4/2003 | Swenson |
| 6,553,998 B2 | 4/2003 | Heaton et al. |
| 6,566,575 B1 | 5/2003 | Stickels et al. |
| 6,566,577 B1 | 5/2003 | Addison et al. |
| 6,626,891 B2 | 9/2003 | Ohmstede |
| 6,627,215 B1 | 9/2003 | Dale et al. |
| 6,648,862 B2 | 11/2003 | Watson |
| 6,680,113 B1 | 1/2004 | Lucast et al. |
| 6,685,681 B2 | 2/2004 | Lockwood et al. |
| 6,693,180 B2 | 2/2004 | Lee et al. |
| 6,695,823 B1 | 2/2004 | Lina et al. |
| 6,752,794 B2 | 6/2004 | Lockwood et al. |
| 6,787,682 B2 | 9/2004 | Gilman |
| 6,814,079 B2 | 11/2004 | Heaton et al. |
| 6,855,135 B2 | 2/2005 | Lockwood et al. |
| 6,856,821 B2 | 2/2005 | Johnson |
| 6,979,324 B2 | 12/2005 | Bybordi et al. |
| 7,070,584 B2 | 7/2006 | Johnson et al. |
| 7,154,017 B2 | 12/2006 | Sigurjonsson et al. |
| 7,402,721 B2 | 7/2008 | Sigurjonsson et al. |
| 7,569,742 B2 | 8/2009 | Haggstrom et al. |
| 7,645,269 B2 | 1/2010 | Zamierowski |
| 7,846,141 B2 | 12/2010 | Weston |
| 8,062,273 B2 | 11/2011 | Weston |
| 8,216,198 B2 | 7/2012 | Heagle et al. |
| 8,251,979 B2 | 8/2012 | Malhi |
| 8,257,327 B2 | 9/2012 | Blott et al. |
| 8,298,197 B2 | 10/2012 | Eriksson et al. |
| 8,398,614 B2 | 3/2013 | Blott et al. |
| 8,449,509 B2 | 5/2013 | Weston |
| 8,529,532 B2 | 9/2013 | Pinto et al. |
| 8,529,548 B2 | 9/2013 | Blott et al. |
| 8,535,296 B2 | 9/2013 | Blott et al. |
| 8,551,060 B2 | 10/2013 | Schuessler et al. |
| 8,568,386 B2 | 10/2013 | Malhi |
| 8,632,523 B2 | 1/2014 | Eriksson et al. |
| 8,679,081 B2 | 3/2014 | Heagle et al. |
| 8,764,732 B2 | 7/2014 | Hartwell |
| 8,834,451 B2 | 9/2014 | Blott et al. |
| 8,926,592 B2 | 1/2015 | Blott et al. |
| 9,017,302 B2 | 4/2015 | Vitaris et al. |
| 9,192,444 B2 | 11/2015 | Locke et al. |
| 9,198,801 B2 | 12/2015 | Weston |
| 9,211,365 B2 | 12/2015 | Weston |
| 9,289,542 B2 | 3/2016 | Blott et al. |
| 9,861,532 B2 * | 1/2018 | Locke ............... A61F 13/025 |
| 9,877,873 B2 * | 1/2018 | Coulthard ......... A61F 13/00055 |
| 9,956,120 B2 * | 5/2018 | Locke ............... A61F 13/00063 |
| 2001/0030304 A1 | 10/2001 | Kohda et al. |
| 2001/0051178 A1 | 12/2001 | Blatchford et al. |
| 2002/0009568 A1 | 1/2002 | Bries et al. |
| 2002/0016346 A1 | 2/2002 | Brandt et al. |
| 2002/0065494 A1 | 5/2002 | Lockwood et al. |
| 2002/0077661 A1 | 6/2002 | Saadat |
| 2002/0090496 A1 | 7/2002 | Kim et al. |
| 2002/0115951 A1 | 8/2002 | Norstrem et al. |
| 2002/0119292 A1 | 8/2002 | Venkatasanthanam et al. |
| 2002/0120185 A1 | 8/2002 | Johnson |
| 2002/0130064 A1 | 9/2002 | Adams et al. |
| 2002/0143286 A1 | 10/2002 | Tumey |
| 2002/0150270 A1 | 10/2002 | Werner |
| 2002/0150720 A1 | 10/2002 | Howard et al. |
| 2002/0161346 A1 | 10/2002 | Lockwood et al. |
| 2002/0164346 A1 | 11/2002 | Nicolette |
| 2002/0183702 A1 | 12/2002 | Henley et al. |
| 2002/0198504 A1 | 12/2002 | Risk et al. |
| 2003/0014022 A1 | 1/2003 | Lockwood et al. |
| 2003/0109855 A1 | 6/2003 | Solem et al. |
| 2003/0158577 A1 | 8/2003 | Ginn et al. |
| 2003/0212357 A1 | 11/2003 | Pace |
| 2003/0225347 A1 | 12/2003 | Argenta et al. |
| 2003/0225355 A1 | 12/2003 | Butler |
| 2004/0002676 A1 | 1/2004 | Siegwart et al. |
| 2004/0030304 A1 | 2/2004 | Hunt et al. |
| 2004/0064132 A1 | 4/2004 | Boehringer et al. |
| 2004/0077984 A1 | 4/2004 | Worthley |
| 2004/0099268 A1 | 5/2004 | Smith et al. |
| 2004/0118401 A1 | 6/2004 | Smith et al. |
| 2004/0127836 A1 | 7/2004 | Sigurjonsson et al. |
| 2004/0127862 A1 | 7/2004 | Bubb et al. |
| 2004/0133143 A1 | 7/2004 | Burton et al. |
| 2004/0186239 A1 | 9/2004 | Qin et al. |
| 2004/0219337 A1 | 11/2004 | Langley et al. |
| 2004/0230179 A1 | 11/2004 | Shehada |
| 2005/0034731 A1 | 2/2005 | Rousseau et al. |
| 2005/0054998 A1 | 3/2005 | Poccia et al. |
| 2005/0059918 A1 | 3/2005 | Sigurjonsson et al. |
| 2005/0065484 A1 | 3/2005 | Watson |
| 2005/0070858 A1 | 3/2005 | Lockwood et al. |
| 2005/0101940 A1 | 5/2005 | Radl et al. |
| 2005/0113732 A1 | 5/2005 | Lawry |
| 2005/0124925 A1 | 6/2005 | Scherpenborg |
| 2005/0131327 A1 | 6/2005 | Lockwood et al. |
| 2005/0137539 A1 | 6/2005 | Biggie et al. |
| 2005/0143694 A1 | 6/2005 | Schmidt et al. |
| 2005/0159695 A1 | 7/2005 | Cullen et al. |
| 2005/0161042 A1 | 7/2005 | Fudge et al. |
| 2005/0163978 A1 | 7/2005 | Strobech et al. |
| 2005/0214376 A1 | 9/2005 | Faure et al. |
| 2005/0233072 A1 | 10/2005 | Stephan et al. |
| 2005/0256437 A1 | 11/2005 | Silcock et al. |
| 2005/0261642 A1 | 11/2005 | Weston |
| 2005/0261643 A1 | 11/2005 | Bybordi et al. |
| 2005/0277860 A1 | 12/2005 | Jensen |
| 2006/0079852 A1 | 4/2006 | Bubb et al. |
| 2006/0083776 A1 | 4/2006 | Bott et al. |
| 2006/0154546 A1 | 7/2006 | Murphy et al. |
| 2006/0236979 A1 | 10/2006 | Stolarz et al. |
| 2006/0241542 A1 | 10/2006 | Gudnason et al. |
| 2006/0271020 A1 | 11/2006 | Huang et al. |
| 2007/0027414 A1 | 2/2007 | Hoffman et al. |
| 2007/0078366 A1 | 4/2007 | Haggstrom et al. |
| 2007/0161937 A1 | 7/2007 | Aali |
| 2007/0185426 A1 | 8/2007 | Ambrosio et al. |
| 2007/0225663 A1 | 9/2007 | Watt et al. |
| 2007/0265585 A1 | 11/2007 | Joshi et al. |
| 2007/0265586 A1 | 11/2007 | Joshi et al. |
| 2008/0027366 A1 | 1/2008 | Da Silva Macedo |
| 2008/0090085 A1 | 4/2008 | Kawate et al. |
| 2008/0119802 A1 | 5/2008 | Riesinger |
| 2008/0138591 A1 | 6/2008 | Graham et al. |
| 2008/0149104 A1 | 6/2008 | Eifler |
| 2008/0173389 A1 | 7/2008 | Mehta et al. |
| 2008/0195017 A1 | 8/2008 | Robinson et al. |
| 2008/0225663 A1 | 9/2008 | Smith et al. |
| 2008/0243044 A1 | 10/2008 | Hunt et al. |
| 2008/0269657 A1 | 10/2008 | Brenneman et al. |

(56) References Cited

U.S. PATENT DOCUMENTS

| | | |
|---|---|---|
| 2008/0271804 A1 | 11/2008 | Biggie et al. |
| 2009/0025724 A1 | 1/2009 | Herron, Jr. |
| 2009/0088719 A1 | 4/2009 | Driskell |
| 2009/0093779 A1 | 4/2009 | Riesinger |
| 2009/0124988 A1 | 5/2009 | Coulthard |
| 2009/0177172 A1 | 7/2009 | Wilkes |
| 2009/0216170 A1 | 8/2009 | Robinson et al. |
| 2009/0216204 A1 | 8/2009 | Bhavaraju et al. |
| 2009/0227969 A1 | 9/2009 | Jaeb et al. |
| 2009/0240185 A1* | 9/2009 | Jaeb ................ A61M 1/0088 602/48 |
| 2009/0264807 A1 | 10/2009 | Haggstrom et al. |
| 2009/0292264 A1 | 11/2009 | Hudspeth et al. |
| 2009/0312662 A1 | 12/2009 | Colman et al. |
| 2009/0326487 A1 | 12/2009 | Vitaris |
| 2009/0326488 A1 | 12/2009 | Budig et al. |
| 2010/0028390 A1* | 2/2010 | Cleary ................ A61B 17/205 424/400 |
| 2010/0063467 A1 | 3/2010 | Addison et al. |
| 2010/0106106 A1 | 4/2010 | Heaton et al. |
| 2010/0106118 A1 | 4/2010 | Heaton et al. |
| 2010/0125259 A1 | 5/2010 | Olson |
| 2010/0159192 A1 | 6/2010 | Cotton |
| 2010/0185163 A1 | 7/2010 | Heagle |
| 2010/0226824 A1 | 9/2010 | Ophir et al. |
| 2010/0262090 A1 | 10/2010 | Riesinger |
| 2010/0267302 A1 | 10/2010 | Kantner et al. |
| 2010/0305490 A1 | 12/2010 | Coulthard et al. |
| 2010/0305524 A1 | 12/2010 | Vess et al. |
| 2010/0318072 A1 | 12/2010 | Johnston et al. |
| 2010/0324516 A1 | 12/2010 | Braga et al. |
| 2011/0046585 A1 | 2/2011 | Weston |
| 2011/0137271 A1 | 6/2011 | Andresen et al. |
| 2011/0160686 A1 | 6/2011 | Ueda et al. |
| 2011/0171480 A1 | 7/2011 | Mori et al. |
| 2011/0172617 A1 | 7/2011 | Riesinger |
| 2011/0224631 A1 | 9/2011 | Simmons et al. |
| 2011/0229688 A1 | 9/2011 | Cotton |
| 2011/0244010 A1 | 10/2011 | Doshi |
| 2011/0257617 A1 | 10/2011 | Franklin |
| 2011/0282309 A1 | 11/2011 | Adie et al. |
| 2012/0016322 A1 | 1/2012 | Coulthard et al. |
| 2012/0019031 A1 | 1/2012 | Bessert |
| 2012/0040131 A1 | 2/2012 | Speer |
| 2012/0123359 A1 | 5/2012 | Reed |
| 2012/0143157 A1 | 6/2012 | Riesinger |
| 2012/0258271 A1 | 10/2012 | Maughan |
| 2013/0030394 A1 | 1/2013 | Locke et al. |
| 2013/0053746 A1 | 2/2013 | Roland et al. |
| 2013/0066285 A1 | 3/2013 | Locke et al. |
| 2013/0096518 A1 | 4/2013 | Hall et al. |
| 2013/0152945 A1 | 6/2013 | Locke et al. |
| 2014/0039423 A1 | 2/2014 | Riesinger |
| 2014/0039424 A1 | 2/2014 | Locke |
| 2014/0141197 A1 | 5/2014 | Hill et al. |
| 2014/0155849 A1 | 6/2014 | Heaton et al. |
| 2014/0163491 A1 | 6/2014 | Schuessler et al. |
| 2014/0171851 A1 | 6/2014 | Addison |
| 2014/0309574 A1 | 10/2014 | Cotton |
| 2014/0350494 A1 | 11/2014 | Hartwell et al. |
| 2014/0352073 A1 | 12/2014 | Goenka |
| 2015/0030848 A1 | 1/2015 | Goubard |
| 2015/0057625 A1* | 2/2015 | Coulthard .......... A61F 13/00068 604/319 |
| 2015/0080788 A1 | 3/2015 | Blott et al. |
| 2015/0119830 A1 | 4/2015 | Luckemeyer et al. |
| 2015/0119833 A1 | 4/2015 | Coulthard et al. |
| 2015/0141941 A1 | 5/2015 | Allen et al. |
| 2015/0190286 A1 | 7/2015 | Allen et al. |
| 2016/0000610 A1 | 1/2016 | Riesinger |
| 2016/0067107 A1 | 3/2016 | Cotton |
| 2016/0144084 A1 | 5/2016 | Collinson et al. |

FOREIGN PATENT DOCUMENTS

| | | |
|---|---|---|
| AU | 755496 B2 | 12/2002 |
| AU | 2009200608 A1 | 10/2009 |
| CA | 2005436 A1 | 6/1990 |
| CN | 87101823 A | 8/1988 |
| DE | 26 40 413 A1 | 3/1978 |
| DE | 43 06 478 A1 | 9/1994 |
| DE | 29 504 378 U1 | 9/1995 |
| DE | 202004018245 U1 | 7/2005 |
| DE | 202014100383 U1 | 2/2015 |
| EP | 0097517 A1 | 1/1984 |
| EP | 0100148 A1 | 2/1984 |
| EP | 0117632 A2 | 9/1984 |
| EP | 0161865 A2 | 11/1985 |
| EP | 0251810 A2 | 1/1988 |
| EP | 0275353 A2 | 7/1988 |
| EP | 0358302 A2 | 3/1990 |
| EP | 0538917 A1 | 4/1993 |
| EP | 0630629 A1 | 12/1994 |
| EP | 0659390 A2 | 6/1995 |
| EP | 0633758 B1 | 10/1996 |
| EP | 1002846 A1 | 5/2000 |
| EP | 1018967 A1 | 7/2000 |
| EP | 2578193 A1 | 4/2013 |
| GB | 692578 A | 6/1953 |
| GB | 1386800 A | 3/1975 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| GB | 2377939 A | 1/2003 |
| GB | 2392836 A | 3/2004 |
| GB | 2393655 A | 4/2004 |
| GB | 2425487 A | 11/2006 |
| GB | 2452720 A | 3/2009 |
| GB | 2496310 A | 5/2013 |
| JP | 1961003393 | 2/1961 |
| JP | S62139523 U | 9/1987 |
| JP | S62-275456 A | 11/1987 |
| JP | 2005205120 A | 8/2005 |
| JP | 2007254515 A | 10/2007 |
| JP | 2008080137 A | 4/2008 |
| JP | 4129536 B2 | 8/2008 |
| SG | 71559 | 4/2002 |
| WO | 80/02182 A1 | 10/1980 |
| WO | 87/04626 A1 | 8/1987 |
| WO | 8707164 A1 | 12/1987 |
| WO | 90/010424 A1 | 9/1990 |
| WO | 93/009727 A1 | 5/1993 |
| WO | 94/020041 A1 | 9/1994 |
| WO | 96/05873 A1 | 2/1996 |
| WO | 9622753 A1 | 8/1996 |
| WO | 97/18007 A1 | 5/1997 |
| WO | 99/13793 A1 | 3/1999 |
| WO | 99/65542 A1 | 12/1999 |
| WO | 01/36188 A1 | 5/2001 |
| WO | 01/60296 A1 | 8/2001 |
| WO | 0168021 A1 | 9/2001 |
| WO | 0185248 A1 | 11/2001 |
| WO | 0190465 A2 | 11/2001 |
| WO | 0243743 A1 | 6/2002 |
| WO | 02062403 A1 | 8/2002 |
| WO | 03-018098 A2 | 3/2003 |
| WO | 03045294 A1 | 6/2003 |
| WO | 03045492 A1 | 6/2003 |
| WO | 03053484 A1 | 7/2003 |
| WO | 2004024197 A1 | 3/2004 |
| WO | 2004037334 A1 | 5/2004 |
| WO | 2004112852 A1 | 12/2004 |
| WO | 2005002483 A2 | 1/2005 |
| WO | 2005062896 A2 | 7/2005 |
| WO | 2005105176 A1 | 11/2005 |
| WO | 2005123170 A1 | 12/2005 |
| WO | 2007022097 A2 | 2/2007 |
| WO | 2007030601 A2 | 3/2007 |
| WO | 2007070269 A1 | 6/2007 |

(56) References Cited

FOREIGN PATENT DOCUMENTS

| WO | 2007085396 A1 | 8/2007 |
|---|---|---|
| WO | 2007087811 A1 | 8/2007 |
| WO | 2007113597 A2 | 10/2007 |
| WO | 2007133618 A2 | 11/2007 |
| WO | 2008026117 A1 | 3/2008 |
| WO | 2008041926 A1 | 4/2008 |
| WO | 2008048527 A2 | 4/2008 |
| WO | 2008054312 A1 | 5/2008 |
| WO | 2008/082444 A2 | 7/2008 |
| WO | 2008/100440 A1 | 8/2008 |
| WO | 2008104609 A1 | 9/2008 |
| WO | 2008/131895 A1 | 11/2008 |
| WO | 2009/002260 A1 | 12/2008 |
| WO | 2008149107 A1 | 12/2008 |
| WO | 2009066105 A1 | 5/2009 |
| WO | 2009066106 A1 | 5/2009 |
| WO | 2009081134 A1 | 7/2009 |
| WO | 2009089016 A1 | 7/2009 |
| WO | 2009/124100 A1 | 10/2009 |
| WO | 2009126103 A1 | 10/2009 |
| WO | 2010016791 A1 | 2/2010 |
| WO | 2010032728 A1 | 3/2010 |
| WO | 2010/056977 A2 | 5/2010 |
| WO | 2010129299 A2 | 11/2010 |
| WO | 2011008497 A2 | 1/2011 |
| WO | 2011/049562 A1 | 4/2011 |
| WO | 2011043786 A1 | 4/2011 |
| WO | 2011115908 A1 | 9/2011 |
| WO | 2011121127 A1 | 10/2011 |
| WO | 2011130570 A1 | 10/2011 |
| WO | 2011162862 A1 | 12/2011 |
| WO | 2012/112204 A1 | 8/2012 |
| WO | 2012104584 A1 | 8/2012 |
| WO | 2012140378 A1 | 10/2012 |
| WO | 2012143665 A1 | 10/2012 |
| WO | 2013009239 A1 | 1/2013 |
| WO | 2013090810 A1 | 6/2013 |
| WO | 2014022400 A1 | 2/2014 |
| WO | 2014039557 A1 | 3/2014 |
| WO | 2014078518 A1 | 5/2014 |
| WO | 2014/113253 A1 | 7/2014 |
| WO | 2014140608 A1 | 9/2014 |
| WO | 2014143488 A1 | 9/2014 |
| WO | 2015/065615 A1 | 5/2015 |
| WO | 2015130471 A1 | 9/2015 |
| WO | 2017048866 A1 | 3/2017 |

OTHER PUBLICATIONS

Extended European Search Report for related application 16793298.7, dated Mar. 27, 2018.
Japanese office action for corresponding application 2015-547246, dated Sep. 5, 2017.
Office Action for related U.S. Appl. No. 13/982,650, dated Dec. 14, 2017.
Australian Office Action for related application 2013344686, dated Nov. 28, 2017.
Office Action for related U.S. Appl. No. 14/517,521, dated Dec. 12, 2017.
Office Action for related U.S. Appl. No. 14/490,898, dated Jan. 4, 2018.
International Search Report and Written Opinion for related appplication PCT/US2017/058209, dated Jan. 10, 2018.
Office Action for related U.S. Appl. No. 14/965,675, dated Jan. 31, 2018.
International Search Report and Written Opinion for related application PCT/US2016/047351, dated Nov. 2, 2016.
M. Waring et al., "Cell attachment to adhesive dressing: qualitative and quantitative analysis", Wounds, UK, (2008), vol. 4, No. 3, pp. 35-47.
R. White, "Evidence for atraumatic soft silicone wound dressing use". Wound, UK (2005), vol. 3, pp. 104-108, Mepilex Border docs, (2001).

European Search Report for corresponding application 17183683.6, dated Sep. 18, 2017.
European Search Report for corresponding application 17164033.7, dated Oct. 13, 2017.
Extended European Search Report for corresponding application 17191970.7, dated Oct. 26, 2017.
European Search Report for corresponding EP Application 171572787 dated Jun. 6, 2017.
International Search Report and Written Opinion for corresponding application PCT/US2016/031397, dated Aug. 8, 2016.
European Search Report for corresponding application 17167872.5, dated Aug. 14, 2017.
Louis C. Argenta, MD and Michael J. Morykwas, PHD; Vacuum-Assisted Closure: A New Method for Wound Control and Treatment: Clinical Experience; Annals of Plastic Surgery.
Susan Mendez-Eatmen, RN; "When wounds Won't Heal" RN Jan. 1998, vol. 61 (1); Medical Economics Company, Inc., Montvale, NJ, USA; pp. 20-24.
James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.
John Masters; "Reliable, Inexpensive and Simple Suction Dressings"; Letter to the Editor, British Journal of Plastic Surgery, 198, vol. 51 (3), p. 267; Elsevier Science/The British Association of Plastic Surgeons, UK.
S.E. Greer, et al. "The Use of Subatmospheric Pressure Dressing Therapy to Close Lymphocutaneous Fistulas of the Groin" British Journal of Plastic Surgery (2000), 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; dated Nov. 23, 1995.
PCT International Search Report for PCT International Application PCT/GB98/02713; dated Jan. 8, 1999.
PCT Written Opinion; PCT International Application PCT/GB98/02713; dated Jun. 8, 1999.
PCT International Examination and Search Report, PCT International Application PCT/GB96/02802; dated Jan. 15, 1998 & Apr. 29, 1997.
PCT Written Opinion, PCT International Application PCT/GB96/02802; dated Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu.N., et al; "Active Wound Drainage", Vestnki Khirurgi, vol. 138, Issue 4, 1987, and 7 page English translation thereof.
Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.
Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E, M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.

(56) References Cited

OTHER PUBLICATIONS

Svedman, P.: "Irrigation Treatment of Leg Ulcers", The Lancet, Sep. 3, 1983, pp. 532-534.
Chinn, Steven D. et al: "Closed Wound Suction Drainage", The Journal of Foot Surgery, vol. 24, No. 1, 1985, pp. 76-81.
Arnljots, Björn et al: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.
N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (copy and certified translation).
F.E. Johnson, "An Improved Technique for Skin Graft Placement Using a Suction Drain," Surgery, Gynecology, and Obstetrics 159 (1984), pp. 584-585
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).
C.E. Tennants, "The Use of Hypermia in the Postoperative Treatment of Lesions of the Extremities and Thorax, "Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C. ® Therapy Clinical Guidelines: A Reference Source for Clinicians; Jul. 2007.
European Search Report for corresponding Application No. 15192606.0 dated Feb. 24, 2016.
International Search Report and Written Opinion for corresponding PCT/US2014/048081 dated Nov. 14, 2014.
International Search Report and Written Opinion for corresponding PCT/US2014/010704 dated Mar. 25, 2014.
European Examination Report dated Jun. 29, 2016, corresponding to EP Application No. 16173614.5.
International Search Report and Written Opinion for PCT/US2014/056508 dated Dec. 9, 2014.
International Search Report and Written Opinion for PCT/GB2008/003075 dated Mar. 11, 2010.
International Search Report and Written Opinion for PCT/GB2008/004216 dated Jul. 2, 2009.
International Search Report and Written Opinion for PCT/GB2012/000099 dated May 2, 2012.
EP Examination Report for corresponding application 12705381.7, dated May 22, 2014.
International Search Report and Written Opinion for PCT/US2012/069893 dated Apr. 8, 2013.
International Search Report and Written Opinion for PCT/US2013/070070 dated Jan. 29, 2014.
International Search Report and Written Opinion for PCT/US2014/016320 dated Apr. 15, 2014.
International Search Report and Written Opinion for PCT/US2014/056566 dated Dec. 5, 2014.
International Search Report and Written Opinion for PCT/US2014/056524 dated Dec. 11, 2014.
International Search Report and Written Opinion for PCT/US2014/056594 dated Dec. 2, 2014.
Partial Internationl Search Report dated Jul. 31, 2009; PCT Internationl Application No. PCT/US2009/036222.
International Search Report and Written opinion dated Dec. 15, 2009; PCT Internation Application No. PCT/US2009/036222.
International Search Report and Written Opinion dated Feb. 24, 2010; PCT/US2009/057182.
International Search Report and Written Opinion dated Jan. 5, 2010; PCT International Application No. PCT/US2009/057130.
Response filed Oct. 20, 2011 for U.S. Appl. No. 12/398,904.
Interview Summary dated Oct. 27, 2011 for U.S. Appl. No. 12/398,904.
Non-Final Office Action dated Jul. 20, 2011 for U.S. Appl. No. 12/398,904.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medican Institute, Gorky, U.S.S.R. 1987) ("Solovev Guidelines").
V.A. Kuznetsov & N.a. Bagautdinov, "Vacuum and Vacuum-Sorption Treatment of Open Septic Wounds," in All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
NDP 1000 Negative Pressure Wound Terapy System, Kalypto Medical, pp. 1-4.
Partial International Search Report dated Jul. 31, 2009 for PCT International Application No. PCT/US2009/036217.
International Search Report and Written Opinion dated May 31, 2010 for PCT Application No. PCT/US2009/064364.
Examination report for AU2009221772 dated Apr. 4, 2013.
Response filed Oct. 21, 2011 for U.S. Appl. No. 12/398,891.
Interview Summary dated Oct. 27, 2011 for U.S. Appl. No. 12/398,891.
Restriction Requirement dated Jun. 13, 2011 for U.S. Appl. No. 12/398,891.
Response filed Jun. 24, 2011 for U.S. Appl. No. 12/398,891.
Non-Final Office Action dated Jul. 21, 2011 for U.S. Appl. No. 12/398,891.
International Search Report and Written Opinion dated Oct. 19, 2010; PCT International Application No. PCT/US2009/036217.
International Search Report and Written Opinion dated Feb. 24, 2010; PCT International Application No. PCT/US2009/057182.
NPD 1000 Negative Pressure Would Therapy System, Kalypto Medical, pp. 1-4.
Partial International Search Report dated Jul. 31, 2009; PCT Internationl Application No. PCT/US2009/036222.
Non-Final Rejection for U.S. Appl. No. 12/398,904 dated Mar. 14, 2012.
Response to Non-Final Rejection for U.S. Appl. No. 12/398,904, filed Jun. 4, 2012.
International Search Report and Written Opinion for PCT/US2014/061251 dated May 8, 2015.

(56) References Cited

OTHER PUBLICATIONS

International Search Report and Written Opinion for PCT/IB2013/060862 dated Jun. 26, 2014.
International Search Report and Written Opinion for PCT/US2015/015493 dated May 4, 2015.
European Search Report for corresponding Application No. 15194949.2.
European Search Report for corresponding EPSN 15157408.4 published on Sep. 30, 2015.
International Search Report and Written Opinion for PCT/US2015/029037 dated Sep. 4, 2015.
International Search Report and Written Opinion for PCT/US2015/034289 dated Aug. 21, 2015.
International Search Report and Written Opinion for PCT/US2015/065135 dated Apr. 4, 2016.
International Search Report and Written Opinion for PCT/GB2012/050822 dated Aug. 8, 2012.
International Search Report and Written Opinion dated Jun. 1, 2011 for PCT International Application No. PCT/US2011/028344.
European Search Report for EP 11714148.1, dated May 2, 2014.
International Search Report and Written Opinion for corresponding PCT application PCT/US2016/051768 dated Dec. 15, 2016.
Office Action for related U.S. Appl. No. 14/965,675, dated Aug. 9, 2018.
Office Action for related U.S. Appl. No. 14/965,675, dated Dec. 12, 2018.
Office Action for related U.S. Appl. No. 14/619,714, dated Dec. 3, 2018.
Office Action for related U.S. Appl. No. 14/630,290, dated Jan. 11, 2019.
Office Action for related U.S. Appl. No. 15/265,718, dated Feb. 7, 2019.
Office Action for related U.S. Appl. No. 15/410,991, dated May 2, 2019.
Extended European Search Report for related application 18193559.4, dated Dec. 17, 2018.
Office Action for related U.S. Appl. No. 14/080,348, dated Apr. 12, 2019.
Japanese Notice of Rejection for related application 2016-570333, dated Feb. 26, 2019.

* cited by examiner

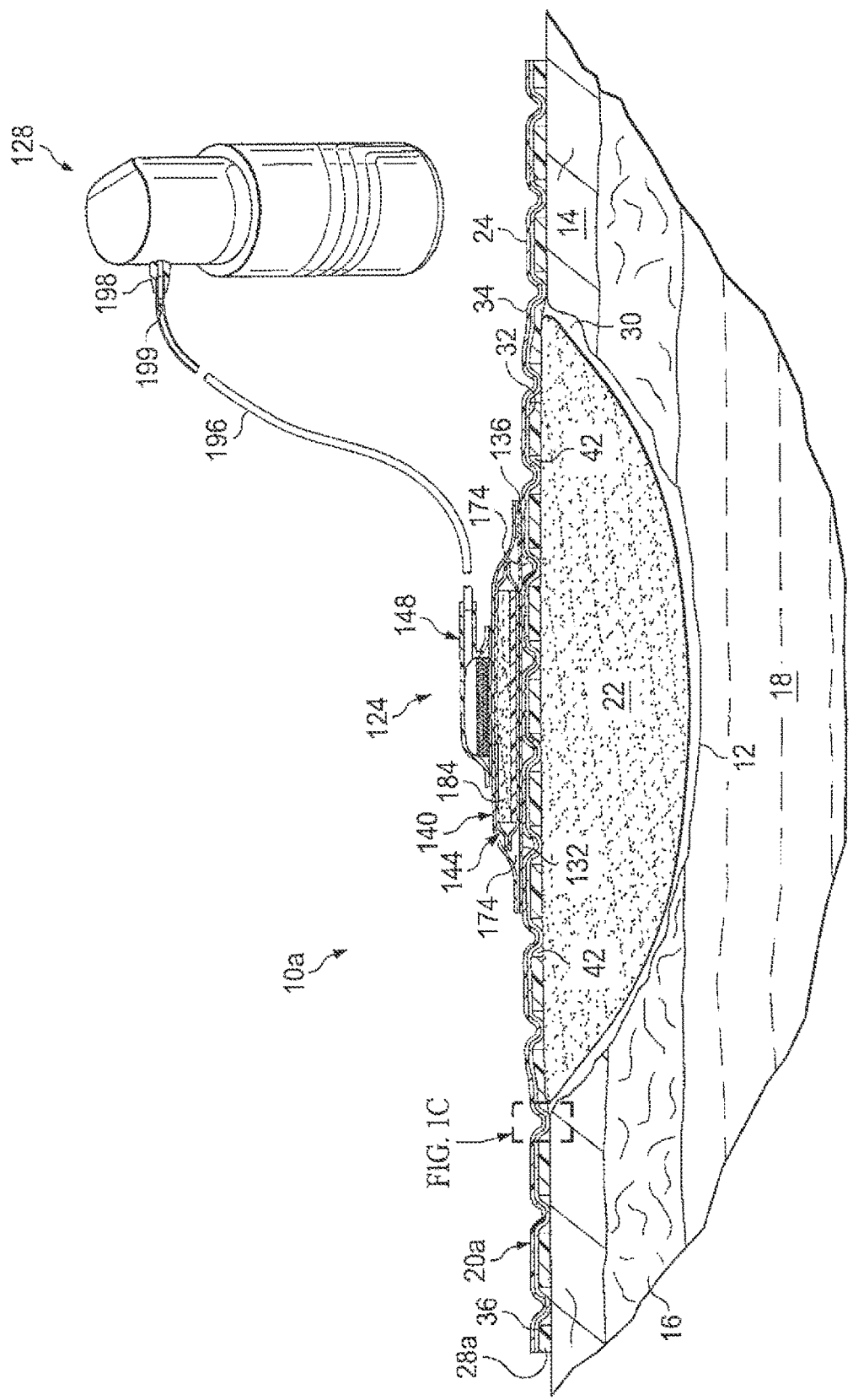

FLUID STORAGE DEVICES, SYSTEMS, AND METHODS

RELATED APPLICATION

This application claims the benefit, under 35 USC § 119(e), of the filing of U.S. Provisional Patent Application No. 61/988,076, entitled "Fluid Storage Devices, Systems, and Methods," filed May 2, 2014, which is incorporated herein by reference for all purposes.

FIELD

This disclosure relates generally to medical treatment systems and, more particularly, but not by way of limitation, to dressings, systems, and methods for treating a tissue site.

BACKGROUND

Depending on the medical circumstances, reduced pressure may be used for, among other things, reduced-pressure therapy to encourage granulation at a tissue site, draining fluids at a tissue site, closing a wound, reducing edema, promoting perfusion, and fluid management. Some dressings, systems, and methods may include a canister or container positioned separate from a dressing for storing fluids drained or extracted from a tissue site for disposal. These containers are often bulky and cumbersome for a patient being treated, and may be prone to leaks and spills. Some dressings, systems, and methods may require frequent replacement of a dressing or other component applied to the skin of a patient, causing the patient irritation or discomfort. Improvements to dressings, systems, and methods that may, without limitation, enhance fluid management for increasing comfort, fluid capacity, ease of use, and the useable life of the dressing and system are desirable.

SUMMARY

Shortcomings with certain aspects of tissue treatment devices, systems, and methods are addressed as shown and described in a variety of illustrative, non-limiting embodiments herein.

In some embodiments, a system for treating a tissue site may include an interface manifold, an interface sealing member, a receiving site, an absorbent layer, and a storage sealing member. The interface manifold may be adapted to be positioned at the tissue site and to provide fluid communication with the tissue site. The interface sealing member may have an interior facing side and an exterior facing side. The interface sealing member may be adapted to provide a sealed treatment space between the interior facing side of the interface sealing member and the tissue site. The interface manifold may be sized for positioning in the sealed treatment space. The receiving site may be positioned at the exterior facing side of the interface sealing member. The absorbent layer may be for positioning at the receiving site. The storage sealing member may be adapted to provide a sealed storage space between the storage sealing member and the receiving site. The absorbent layer may be sized for positioning in the sealed storage space.

In some embodiments, an interface sealing member for treating a tissue site may include a liquid impermeable material and a receiving site. The liquid impermeable material may have an interior facing side and an exterior facing side positioned opposite the interior facing side. The liquid impermeable material may be adapted to cover the tissue site and to provide a sealed treatment space between the interior facing side of the liquid impermeable material and the tissue site. The receiving site may be positioned at the exterior facing side of the liquid impermeable material. The receiving site may comprise a non-adherent treatment.

In some embodiments, a method of treating a tissue site may include positioning an interface dressing on the tissue site and in fluid communication with the tissue site. The method may also include releaseably securing a storage dressing to the interface dressing and in fluid communication with the interface dressing; and applying reduced pressure to the storage dressing. Further, the method may include extracting fluid from the tissue site through the interface dressing. The storage dressing may be in fluid communication with the tissue site through the interface dressing. The method may additionally include storing fluid extracted from the interface dressing within the storage dressing.

Other aspects, features, and advantages of the illustrative embodiments will become apparent with reference to the drawings and detailed description that follow.

BRIEF DESCRIPTION OF THE DRAWINGS

FIG. 1A is a cut-away view of an illustrative embodiment of a system for treating a tissue site depicting an illustrative embodiment of an interface dressing and a storage dressing deployed at the tissue site;

DETAILED DESCRIPTION OF ILLUSTRATIVE EMBODIMENTS

Figure 1B:
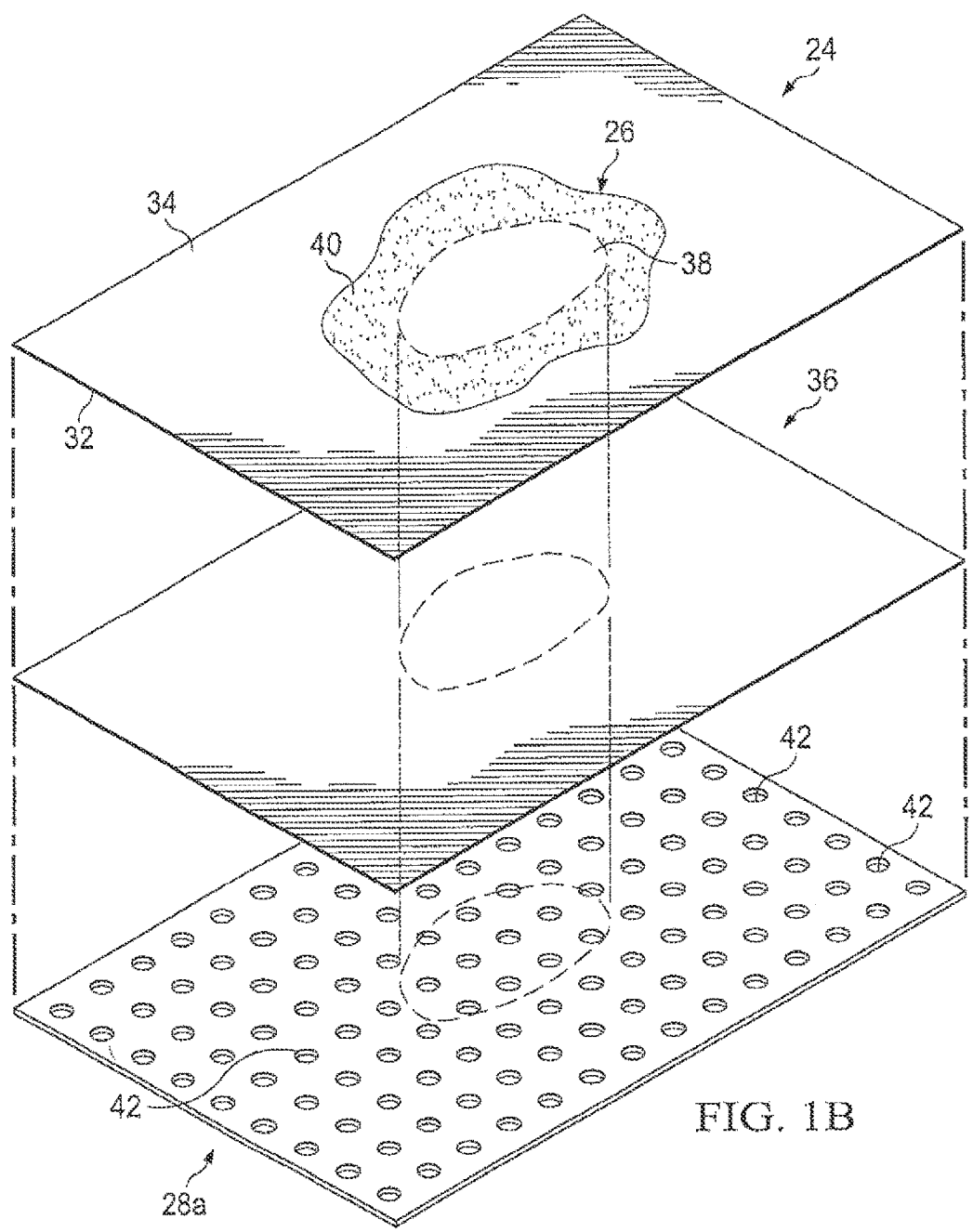
FIG. 1B is an exploded, perspective view of an illustrative embodiment of an interface sealing member depicted in FIG. 1A.

In the following detailed description of non-limiting, illustrative embodiments, reference is made to the accompanying drawings that form a part hereof. Other embodiments may be utilized, and logical, structural, mechanical, electrical, and chemical changes may be made without departing from the scope of the appended claims. To avoid detail not necessary to enable those skilled in the art to practice the embodiments described herein, the description may omit certain information known to those skilled in the art. The following detailed description is non-limiting, and the scope of the illustrative embodiments are defined by the appended claims. As used herein, unless otherwise indicated, "or" does not require mutual exclusivity.

Referring to the drawings, FIG. 1A depicts an illustrative embodiment of a system 10a for treating a tissue site 12 of a patient. FIG. 2A depicts another illustrative embodiment of a system 10b for treating the tissue site 12. The system 10a and the system 10b may be referred to collectively as a system 10 for treating the tissue site 12. The tissue site 12 may extend through or otherwise involve an epidermis 14, a dermis 16, and a subcutaneous tissue 18. The tissue site 12 may be a sub-surface tissue site as depicted in FIGS. 1A and 2A that extends below the surface of the epidermis 14. Further, the tissue site 12 may be a surface tissue site (not shown) that predominantly resides on the surface of the epidermis 14, such as, for example, an incision. The system 10 may provide therapy to, for example, the epidermis 14, the dermis 16, and the subcutaneous tissue 18, regardless of the positioning of the system 10 or the type of tissue site.

The system 10 may also be utilized without limitation at other tissue sites. For example, the tissue site 12 may be, without limitation, the bodily tissue of any human, animal, or other organism, including bone tissue, adipose tissue, muscle tissue, dermal tissue, vascular tissue, connective tissue, cartilage, tendons, ligaments, or any other tissue. The treatment of tissue site 12 may include removal of fluids, such as exudate or ascites.

Referring to the embodiment of FIG. 1A, the system 10a may include a first dressing or interface dressing 20a. Referring to the embodiment of FIG. 2A, the system 10b may include a first dressing or interface dressing 20b. The interface dressing 20a and 20b may be referred to collectively as the interface dressing 20. The interface dressing 20 may include a tissue interface or interface manifold 22 and an interface sealing member 24, in some embodiments, the interface dressing 20 may include a receiving site 26 and an interface base layer 28.

Referring generally to FIGS. 1A-2B, the interface manifold 22 may be adapted to be positioned proximate to, adjacent, or at the tissue site 12, such as, for example, by cutting or otherwise shaping the interface manifold 22 in any suitable manner to fit the tissue site 12. Further, the interface manifold 22 may be adapted to be positioned in fluid communication with the tissue site 12 and may distribute reduced pressure to the tissue site 12, in some embodiments, the interface manifold 22 may be positioned in direct contact with the tissue site 12.

The interface manifold 22 may be formed from any manifold material or flexible bolster material that provides a vacuum space, or treatment space, such as, for example, a porous and permeable foam or foam-like material, a member formed with pathways, a graft, or a gauze. In some embodiments, the interface manifold 22 may be a reticulated, open-cell polyurethane or polyether foam that allows good permeability of fluids. One such foam material is the VAC® GranuFoam® material available from Kinetic Concepts, Inc. (KCI) of San Antonio, Tex. In some embodiments, the interface manifold 22 may comprise a porous, hydrophobic material. The hydrophobic characteristics of the interface manifold 22 may prevent the interface manifold 22 from directly absorbing fluid, such as exudate, from the tissue site 12, hut allow the fluid to pass through.

A material with a higher or lower density than Granu-Foam® material may be desirable for the interface manifold 22, depending on the application. Among the many possible materials, the following may be used without limitation: GranuFoam® material, Foamex® technical foam (www.foamex.com), a molded bed of nails structure, a patterned grid material such as those manufactured by Sercol Industrial Fabrics, 3D textiles such as those manufactured by Baltex of Derby, U.K., a gauze, a flexible channel-containing member, and a graft.

In some embodiments, any material or combination of materials may be used as a manifold material for the interface manifold 22 provided that the manifold material is operable to distribute or collect fluid. For example, the term manifold may refer to a substance or structure capable of delivering fluids to or removing fluids from a tissue site through a plurality of pores, pathways, or flow channels. The plurality of pores, pathways, or flow channels may be interconnected to improve distribution of fluids provided to and removed from an area around the manifold. Examples of such manifolds may include, without limitation, devices that have structural elements arranged to form flow channels, cellular foam, such as open-cell foam, porous tissue collections, and liquids, gels, and foams that include or cure to include flow channels. In some embodiments, the interface manifold 22 may be enhanced with ionic silver and antimicrobial agents.

The interface sealing member 24 may be adapted to cover the tissue site 12 and to provide a fluid seal and a sealed treatment space 30 relative to the tissue site 12. A portion of the interface sealing member 24 may overlap tissue surrounding the tissue site 12, such as the epidermis 14. The interface manifold 22 may be sized or otherwise adapted to be positioned in the sealed treatment space 30. For example, the interface sealing member 24 may include an interior facing side 32 and an exterior facing side 34 positioned opposite the interior facing side 32. The sealed treatment space 30 may be provided between the interior facing side 32 of the interface sealing member 24 and the tissue site 12. In some embodiments, the interface sealing member 24 may comprise a liquid impermeable material adapted to cover the tissue site 12 and tissue surrounding the tissue site 12.

The interface sealing member 24 may be formed from any material that allows for a fluid seal. A fluid seal may be a seal adequate to maintain reduced pressure, if applicable, at a desired site. The interface sealing member 24 may comprise, for example, one or more of the following materials: hydrophilic polyurethane; cellulosics; hydrophilic polyamides; polyvinyl alcohol; polyvinyl pyrrolidone; hydrophilic acrylics; hydrophilic silicone elastomers; an INSPIRE 2301 material from Expopack Advanced Coatings of Wrexham, United Kingdom having for example, a moisture vapor transmission rate or MVTR (Inverted cup technique) of 14400 g/m²/24 hours and a thickness of about 30 microns; a thin, uncoated polymer drape; natural rubbers; polyisoprene; styrene butadiene rubber; chloroprene rubber; polybutadiene; nitrile rubber; butyl rubber; ethylene propylene rubber; ethylene propylene diene monomer; chlorosulfonated polyethylene; polysulfide rubber; polyurethane (PU); EVA film; co-polyester; silicones; a silicone drape; a 3M Tegaderm® drape; a polyurethane (PU) drape such as one available from Avery Dennison Corporation of Pasadena, Calif.; polyether block polyamide copolymer (PEBAX), for example, from Arkema, France; Expopack 2327; or other appropriate material.

The interface sealing member 24 may be vapor permeable and liquid impermeable, thereby allowing vapor and inhibiting liquids from exiting the sealed treatment space 30 provided by the interface dressing 20. In some embodiments, the interface sealing member 24 may be a flexible, breathable film, membrane, or sheet having a high MVTR of, for example, at least about 300 g/m$^2$ per 24 hours. The use of a high MVTR material for the interface sealing member 24 may permit moisture vapor to pass through the interface sealing member 24, external to the interface dressing 20, while maintaining the fluid seal described above. In other embodiments, a low or no vapor transfer drape might be used. The interface sealing member 24 may comprise a range of medically suitable films having a thickness between about 15 microns (μm) to about 50 microns (μm).

In some embodiments, an attachment device or interface layer adhesive 36 may be adapted to be positioned between the interface sealing member 24 and the tissue site 12. For example, the interface layer adhesive 36 may be positioned on or applied to the interior facing side 32, of the interface sealing member 24 for facing the tissue site 12. In some embodiments, the interface sealing member 24 may be sealed directly against tissue surrounding the tissue site 12, such as the epidermis 14, by the interface layer adhesive 36. In some embodiments, the interface layer adhesive 36 may seal the interface sealing member 24 against a gasket or drape adapted to be positioned between the interface layer adhesive 36 and the epidermis 14.

The interface layer adhesive 36 may be a medically-acceptable adhesive and may take numerous forms, such as an adhesive sealing tape, drape tape, paste, hydrocolloid, hydrogel, or other suitable sealing device. The interface layer adhesive 36 may also be flowable. The interface layer adhesive 36 may comprise, without limitation, an acrylic adhesive, rubber adhesive, high-tack silicone adhesive, polyurethane, or other adhesive substance. In some embodiments, the interface layer adhesive 36 may be a pressure-sensitive adhesive comprising an acrylic adhesive with coat weight of 15 grams/m$^2$ (gsm) to 70 grams/m$^2$ (gsm). The pressure-sensitive adhesive may be applied on a side of the interface sealing member 24 adapted to face the epidermis 14 and the tissue site 12, such as the interior facing side 32 of the interface sealing member 24. The pressure-sensitive adhesive may provide a fluid seal between the interface sealing member 24 and the epidermis 14, and may be utilized in combination with a gasket or drape against the epidermis 14.

In some embodiments, the interface layer adhesive 36 may be a layer or coating applied to or positionable on the interior facing side 32 of the interface sealing member 24. In some embodiments, the interface layer adhesive 36 may be continuous or discontinuous. Discontinuities in the interface layer adhesive 36 may be provided by apertures (not shown) in the interface layer adhesive 36. The apertures or discontinuities in the interface layer adhesive 36 may be, for example, formed after application of the interface layer adhesive 36, or by coating the interface layer adhesive 36 in patterns on the interior facing side 32 of the interface sealing member 24.

Figure 2A:
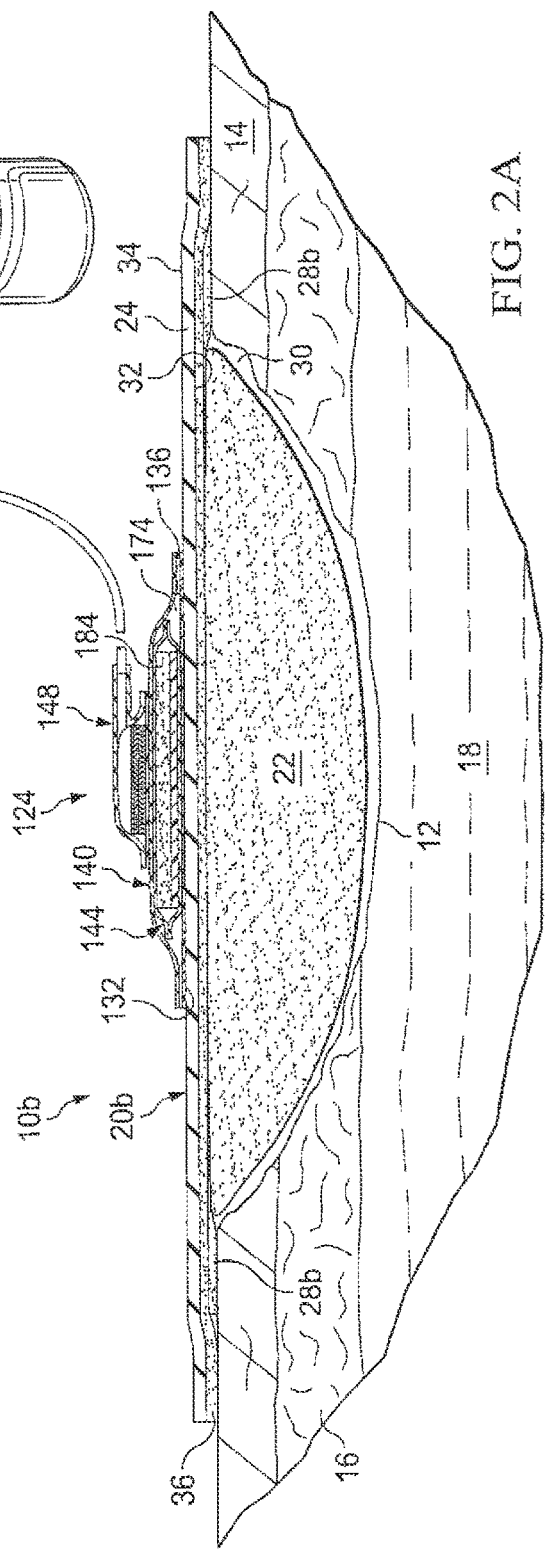
FIG. 2A is a cut-away view of another illustrative embodiment of a system for treating a tissue site depicting another illustrative embodiment of an interface dressing and a storage dressing deployed at the tissue site.
Figure 2B:
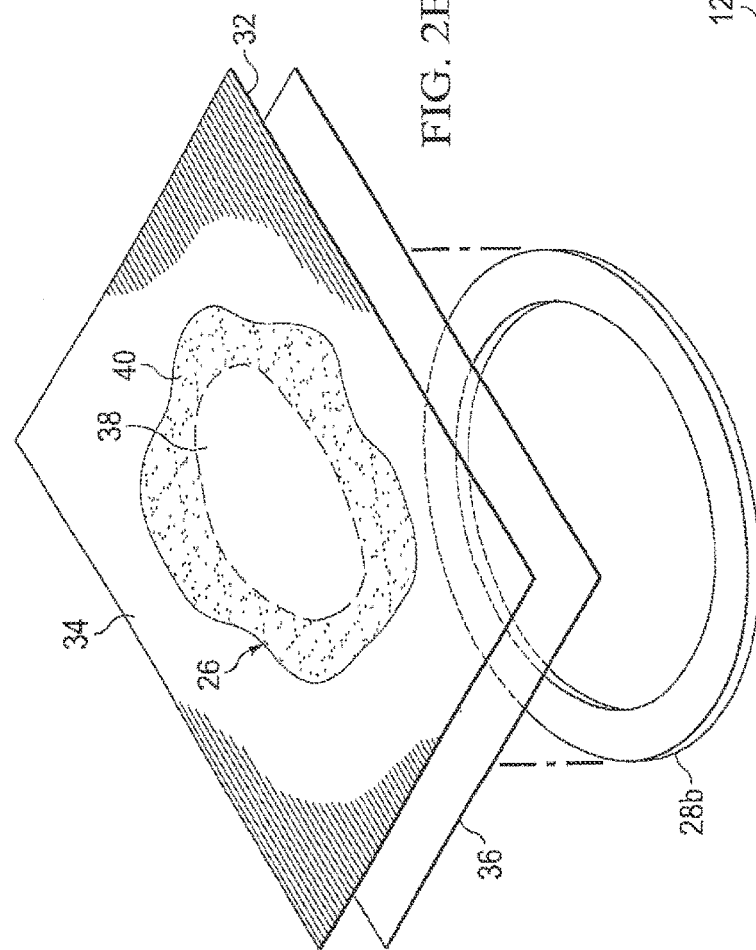
FIG. 2B is an exploded, perspective view of another illustrative embodiment of an interface sealing member depicted in FIG. 2A.

Referring to FIGS. 1B and 2B, in some embodiments, the receiving site 26 may be positioned at or on the exterior facing side 34 of the interface sealing member 24. A portion of the receiving site 26 may be adaptable for providing fluid communication between the exterior facing side 34 and the interior facing side 32 of the interface sealing member 24. For example, the receiving site 26 may be in fluid communication with the interface manifold 22 and the sealed treatment space 30 through a receiving site aperture 38 that may be disposed through the interface sealing member 24.

In some embodiments, the receiving site 26 may comprise a non-adherent treatment 40. The non-adherent treatment 40 may substantially or entirely surround the receiving site aperture 38. Although FIGS. 1B and 2B depict the non-adherent treatment 40 as partially covering the exterior facing side 34 of the interface sealing member 24, the non-adherent treatment 40 may be applied to the entire exterior facing side 34 in some embodiments. The non-adherent treatment 40 may be adapted to releaseably or non-permanently secure components of the system 10 to the receiving site 26. For example, the non-adherent treatment 40 may reduce or impair the bond strength of components of the system 10 being applied to the receiving site 10. In some embodiments, the non-adherent treatment 40 may comprise a coating of a non-adherent material including, without limitation, an olefinic coating, such as a polyethylene or wax; a fluorocarbon coating, such as a polytetrafluoroethylene (PTFE); a highly hydrophilic coating, such as a water soluble or swelling polymer that would retain a high level of moisture capable of reducing bond strength; a coating containing a plasticizer capable of reducing the tackiness of an acrylic or other adhesive; and an ultraviolet (UV) light sensitive coating capable of cross-linking and becoming brittle under the action of UV light. In other embodiments, the substrate material of the interface sealing member 24 on the exterior facing side 34 may be treated or otherwise modified to have non-adherent properties.

The interface base layer 28 may be adapted to be positioned on the interior facing side 32 of the interface sealing member 24 and between the interface sealing member 24 and the tissue site 12. The interface base layer 28 may enhance the fluid seal between the interface sealing member 24 and the tissue site 12. The interface base layer 28 may be a soft, pliable material suitable for providing a fluid seal with the tissue site 12 as described herein. For example, the interface base layer 28 may comprise, without limitation, a silicone gel, a soft silicone, hydrocolloid, hydrogel, polyurethane gel, polyolefin gel, hydrogenated styrenic copolymer gel, a foamed gel, a soft closed cell foam such as polyurethanes and polyolefins that may be coated with an adhesive, polyurethane, polyolefin, and hydrogenated styrenic copolymers, in some embodiments, the interface base layer 28 may have a thickness between about 500 microns (μm) and about 1000 microns (μm). In some embodiments, the interface base layer 28 may have a stiffness between about 5 Shore OO to about 80 Shore OO. Further, the interface base layer 28 may be comprised of hydrophobic or hydrophilic materials.

Figure 1C:
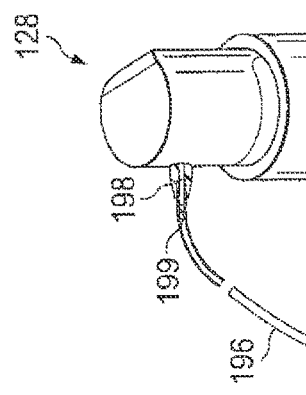
FIG. 1C is detail view taken at reference FIG. 1C, depicted in FIG. 1A, illustrating the interface dressing of FIG. 1A positioned proximate to tissue surrounding the tissue site.

Referring to FIGS. 1A-1C, in some embodiments, the interface base layer 28 may be an interface base layer 28a. Similar to the interface sealing member 24, the interface base layer 28a may be adapted to cover the tissue site 12. A portion of the interface base layer 28a may be adapted to overlap tissue surrounding the tissue site 12, such as the epidermis 14, or otherwise surround the tissue site 12. The interface base layer 28a may include a plurality of interface layer apertures 42 disposed through opposing sides of the interface base layer 28a. The interface layer apertures 42 may be adapted to be in fluid communication with the sealed treatment space 30, the interface manifold 22, and tissue surrounding the tissue site 12, such as the epidermis 14. The interface layer adhesive 36 may be positioned between the interface sealing member 24 and the interface base layer 28a in fluid communication with tissue surrounding the tissue site 12 through the interface layer apertures 42.

The interface layer apertures 42 in the interface base layer 28a may have any shape, such as, for example, circles, squares, stars, ovals, polygons, slits, complex curves, rectilinear shapes, triangles, or other shapes. The interface layer apertures 42 may be formed by cutting, by application of local RF energy, or other suitable techniques for forming an opening. The interface layer apertures 42 may have a diameter between about 6 millimeters to about 50 millimeters. Further, the interface layer apertures 42 may be uniformly distributed or randomly distributed on the interface base layer 28a.

The interface layer adhesive 36 may be in fluid communication with the interface layer apertures 42 of the interface base layer 28a. In this manner, the interface layer adhesive 36 may be in fluid communication with tissue surrounding the tissue site 12 through the interface layer apertures 42 in the interface base layer 28a. As shown in FIG. 1C, the interface layer adhesive 36 may extend or be pressed through the interface layer apertures 42 to contact, for example, the epidermis 14 for securing the interface dressing 20a to tissue surrounding the tissue site 12. The interface layer apertures 42 may provide sufficient contact of the interface layer adhesive 36 to the epidermis 14 to secure the interface dressing 20a about the tissue site 12. However, the configuration of the interface layer apertures 42 and the interface layer adhesive 36, described further below, may permit release and repositioning of the interface dressing 20a about the tissue site 12.

Factors that may be utilized to control the adhesion strength of the interface dressing 20a about the tissue site 12 may include the size and number of the interface layer apertures 42, the thickness of the interface base layer 28a, the thickness and amount of the interface layer adhesive 36, and the tackiness of the interface layer adhesive 36. For example, an increase in the amount of the interface layer adhesive 36 extending through the interface layer apertures 42 may correspond to an increase in the adhesion strength of the interface dressing 20a. Further, a decrease in the thickness of the interface base layer 28a may correspond to an increase in the amount of interface layer adhesive 36 extending through the interface layer apertures 42. Thus, the size and configuration of the interface layer apertures 42, the thickness of the interface base layer 28a, and the amount and tackiness of the interface layer adhesive 36 may be varied to provide a desired adhesion strength for the interface dressing 20a. In some embodiments, the thickness of the interface base layer 28a may be about 200 microns, the interface layer adhesive 36 may have a thickness of about 30 microns and a tackiness of 2000 grams per 25 centimeter wide strip, and the diameter of the interface layer apertures 42 may be about 6 millimeters.

In some embodiments (not shown), the interface base layer 28a may be a hydrophobic-coated material. For example, the interface base layer 28a may be formed by coating a spaced material, such as, for example, a woven, nonwoven, molded, or extruded mesh with a hydrophobic material. The hydrophobic material for the coating may be a soft silicone, for example. In this manner, the interface layer adhesive 36 may extend through openings in the spaced material analogous to the interface layer apertures 42 described above.

Referring to FIGS. 2A-2C, in some embodiments, the interface base layer 28 may be an interface base layer 28b. The interface base layer 28b may be, for example, formed in the shape of a ring or any other suitable shape for surrounding the tissue site 12. While reference is made to a "ring," discrete members, including linear members, may make up the interface base layer 28b in any suitable manner. A ring-like or other suitable shape for the interface base layer 28b may save costs by reducing or eliminating material covering the tissue site 12 while still enhancing the fluid seal around the tissue site 12. For example, tissue surrounding the tissue site 12, such as the epidermis 14, may have recesses, cracks, wrinkles, or other discontinuities that may cause leaks. Moreover, folds, buckles, wrinkles, or other discontinuities may form in the interface sealing member 24 and cause leaks. The interface base layer 28b may reduce any leakage caused by such discontinuities around the tissue site 12.

The interface base layer 28b may be formed, as an illustrative example, by applying or bonding a continuous or discontinuous ring of any of the materials recited above for the interface base layer 28 around the tissue site 12 or to a portion of the interior facing side 32 of the interface sealing member 24 for positioning between the interface sealing member 24 and tissue surrounding the tissue site 12. The interface base layer 28b may be coupled directly to the interface sealing member 24 and tissue surrounding the tissue site 12, or by the interface layer adhesive 36 described above. In some embodiments, the interface base layer 28b may comprise, without limitation, hydrocolloids; hydrogels; silicone polymers; crosslinked and uncrosslinked gels; and natural gums such as xanthan, guar, and cellulose. The interface base layer 28b may include other soft polymer gels, such as, for example, those based on polyurethanes, polyolefin gels, and acrylics.

In some embodiments, the interface base layer 28b may include an absorbent. The absorbent may permit the interface base layer 28b to absorb fluid from the tissue site 12 in addition to enhancing the fluid seal around the tissue site 12. The interface base layer 28b including the absorbent may enhance the ability of the interface dressing 20b to manage and direct fluid away from the tissue site 12 for keeping the tissue site 12 dry. For example, the interface base layer 28b may be a hydrocolloid comprising an absorbent, such as carboxy methyl cellulose (CMC). The absorbent in the interface base layer 28b may wick or draw fluid in a lateral direction within the interface dressing 20b, normal to the thickness of the interface dressing 20b, and toward the lateral edges of the interface dressing 20b for absorption in the interface base layer 28b.

Referring to FIGS. 1A-3, the system 10 may include a second dressing or storage dressing 124, and a reduced-pressure source 128. The storage dressing 124 may be positioned in fluid communication with the interface dressing 20 at, for example, the receiving site 26 of the interface sealing member 24. The storage dressing 124 may be adapted to provide reduced pressure from the reduced-pressure source 128 to the interface manifold 22, and to store fluid extracted from the tissue site 12 through the interface manifold 22. In some embodiments, reduced pressure may not be applied, and fluid may be extracted from the tissue site 12 into the storage dressing 124 by wicking action.

The storage dressing 124 may include a storage base layer 132, a storage layer adhesive 136, a storage sealing member 140, a fluid management assembly 144, and a conduit interface 148. Components of the storage dressing 124 may be added or removed to suit a particular application.

Figure 3:
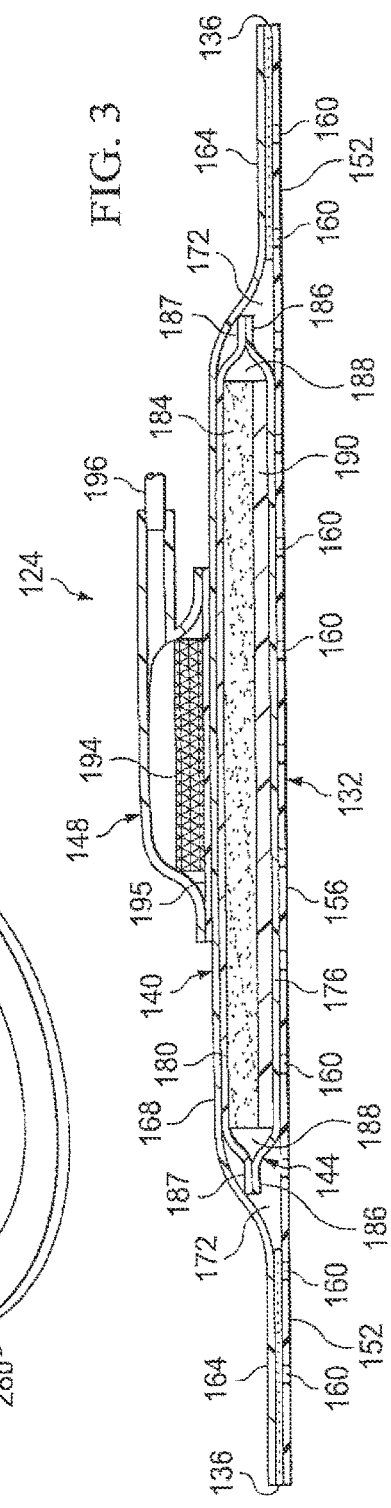
FIG. 3 is a cut-away view of the storage dressing of FIGS. 1A and 2A.
Figure 4A:
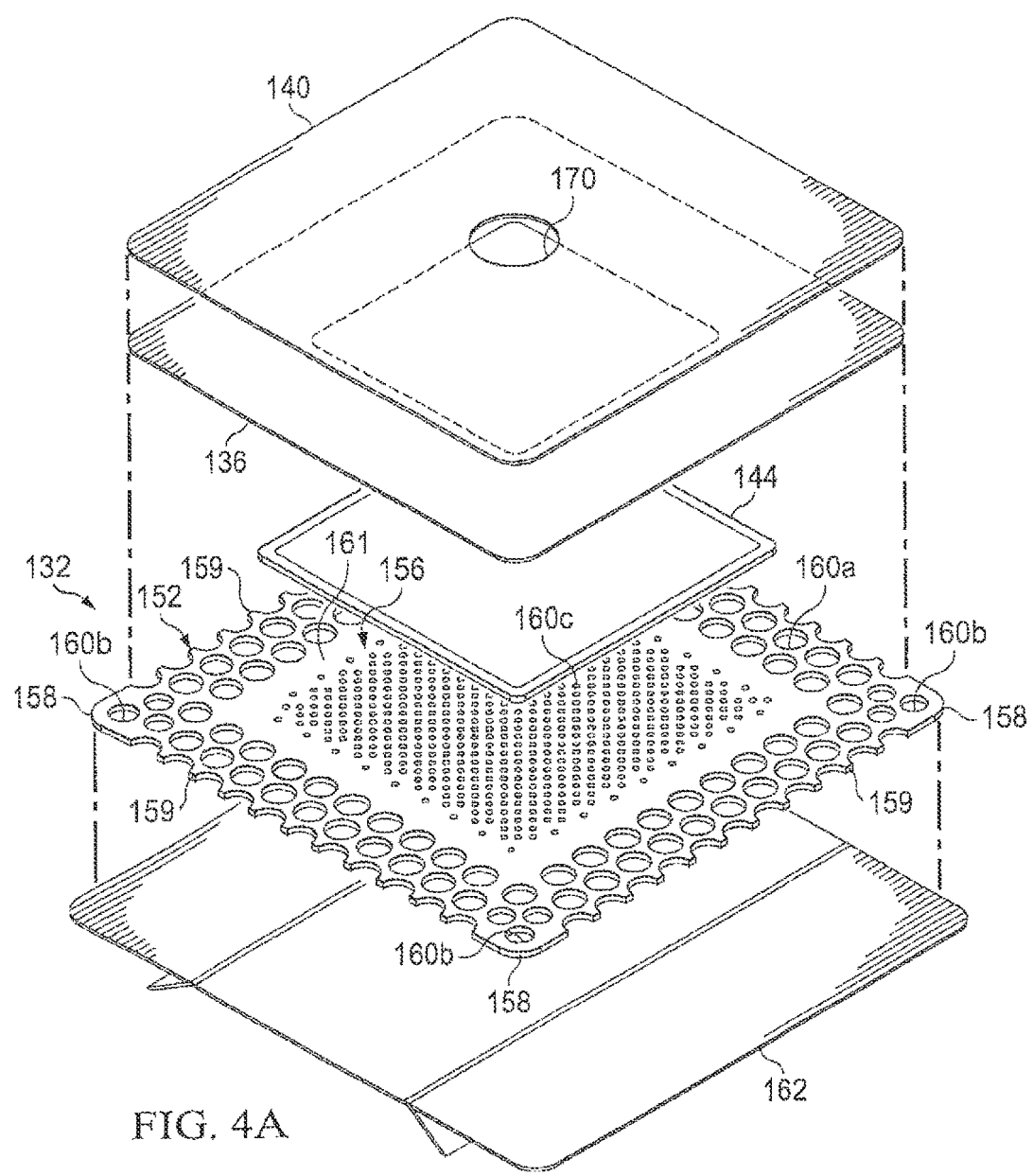
FIG. 4A is an exploded, perspective view of the storage dressing of FIG. 3, depicted without a conduit interface and with an illustrative embodiment of a release liner for protecting the storage dressing prior to application at a tissue site.
Figure 4B:
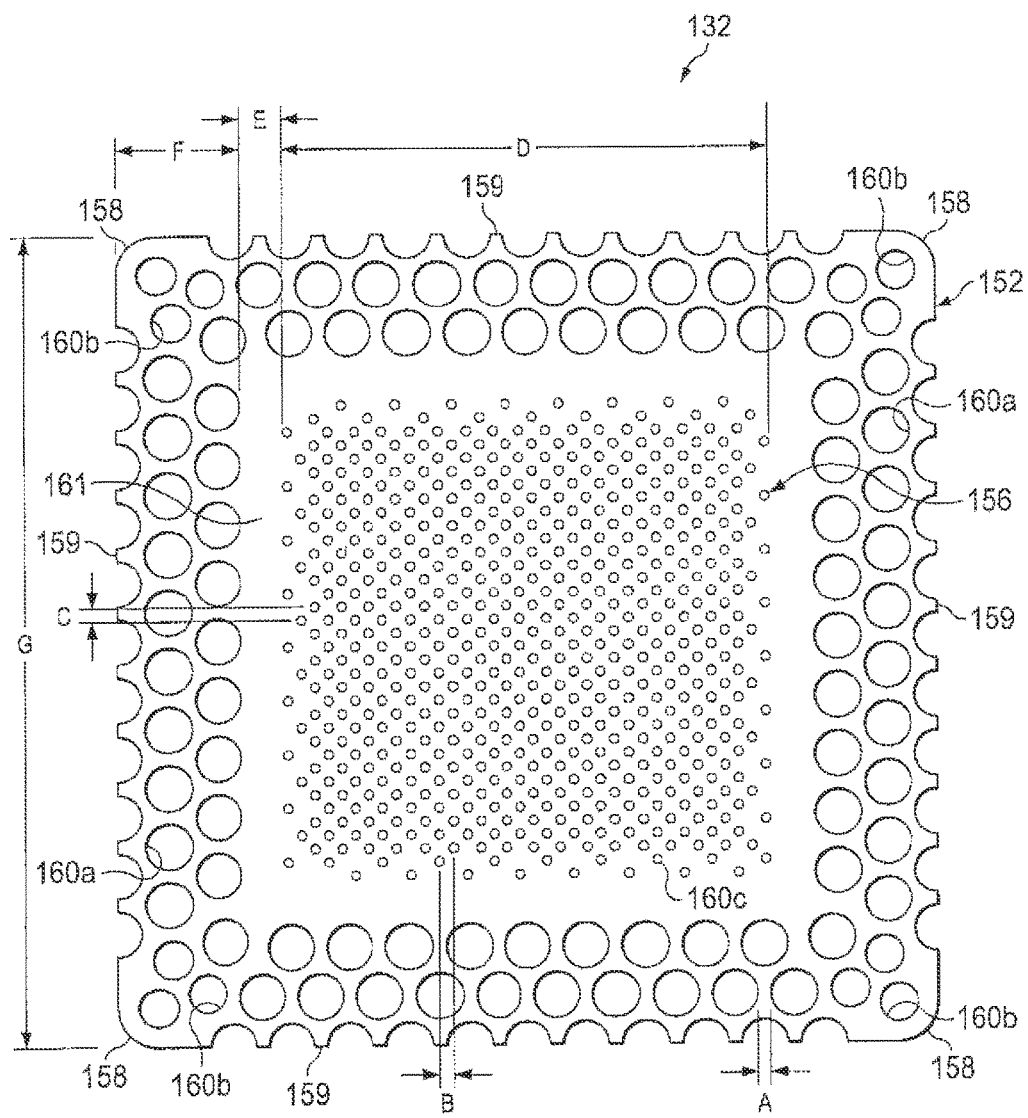
FIG. 4B is a plan view of an illustrative embodiment of a base layer depicted in the storage dressing of FIG. 4A.

Referring to FIGS. 3-4B, the storage base layer 132 may have a periphery 152 surrounding a central portion 156. A plurality of storage layer apertures 160 may be disposed through opposing sides of the storage base layer 132 and through the periphery 152 and the central portion 156. The storage base layer 132 may also have corners 158 and edges 159. The corners 158 and the edges 159 may be part of the periphery 152. One of the edges 159 may meet another of the edges 159 to define one of the corners 158. Further, the storage base layer 132 may have a border 161 substantially surrounding the central portion 156 and positioned between the central portion 156 and the periphery 152. The border 161 may be free of the storage layer apertures 160.

The storage base layer 132 may cover a portion of the exterior facing side 34 of the interface sealing member 24. For example, the central portion 156 of the base layer 132 may be positioned adjacent to or proximate to the receiving site aperture 38, and the periphery 152 of the base layer 132 may be positioned adjacent to or proximate to the receiving site 26 around the receiving site aperture 38. In this manner, the periphery 152 of the storage base layer 132 may surround the receiving site aperture 38. Further, the storage layer apertures 160 in the storage base layer 132 may be in fluid communication with the receiving site aperture 38 and portions of the receiving site 26 surrounding the receiving site aperture 38.

Similar to the interface layer apertures 42, the storage layer apertures 160 in the storage base layer 132 may have any shape, such as, for example, circles, squares, stars, ovals, polygons, slits, complex curves, rectilinear shapes, triangles, or other shapes. The storage layer apertures 160 may be formed by cutting, by application of local RF energy, or other suitable techniques for forming an opening.

As shown in FIGS. 4A-4B, each of the storage layer apertures 160 of the plurality of storage layer apertures 160 may be substantially circular in shape, having a diameter and an area. The area of each of the storage layer apertures 160 may refer to an open space or open area defining each of the storage layer apertures 160. The diameter of each of the storage layer apertures 160 may define the area of each of the storage layer apertures 160. For example, the area of one of the storage layer apertures 160 may be defined by multiplying the square of half the diameter of the storage layer aperture 160 by the value 3.14. Thus, the following equation may define the area of one of the storage layer apertures 160: Area=3.14*(diameter/2)^2.

The area of the storage layer apertures 160 described in the illustrative embodiments herein may be substantially similar to the area in other embodiments (not shown) for the storage layer apertures 160 that may have non-circular shapes. The diameter of each of the storage layer apertures 160 may be substantially the same, or each of the diameters may vary depending, for example, on the position of the storage layer aperture 160 in the storage base layer 132. For example, the diameter of the storage layer apertures 160 in the periphery 152 of the storage base layer 132 may be larger than the diameter of the storage layer apertures 160 in the central portion 156 of the storage base layer 132. Further, the diameter of each of the storage layer apertures 160 may be between about 1 millimeter to about 50 millimeters. In some embodiments, the diameter of each of the storage layer apertures 160 may be between about 1 millimeter to about 20 millimeters. The storage layer apertures 160 may have a uniform pattern or may be randomly distributed on the storage base layer 132. The size and configuration of the storage layer apertures 160 may be designed to control the adherence of the storage dressing 124 to the receiving site 26 of the interface sealing member 24 as described below.

Continuing with FIGS. 4A-4B, in some embodiments, the storage layer apertures 160 positioned in the periphery 152 may be storage layer apertures 160a, the storage layer apertures 160 positioned at the corners 158 of the periphery 152 may be storage layer apertures 160b, and the storage layer apertures 160 positioned in the central portion 156 may be storage layer apertures 160c. The storage layer apertures 160a may have a diameter between about 9.8 millimeters to about 10.2 millimeters. The storage layer apertures 160b may have a diameter between about 7.75 millimeters to about 8.75 millimeters. The storage layer apertures 160c may have a diameter between about 1.8 millimeters to about 2.2 millimeters. The diameter of each of the storage layer apertures 160a may be separated from one another by a distance A between about 2.8 millimeters to about 3.2 millimeters. Further, the diameter of at least one of the storage layer apertures 160a may be separated from the diameter of at least one of the storage layer apertures 160b by the distance A. The diameter of each of the storage layer apertures 160b may also be separated from one another by the distance A. A center of one of the storage layer apertures 160c may be separated from a center of another of the storage layer apertures 160c in a first direction by a distance B between about 2.8 millimeters to about 3.2 millimeters. In a second direction transverse to the first direction, the center of one of the storage layer apertures 160c may be separated from the center of another of the storage layer apertures 160c by a distance C between about 2.8 millimeters to about 3.2 millimeters. As shown in FIGS. 4A-4B, the distance B and the distance C may be increased for the storage layer apertures 160c in the central portion 156 being positioned proximate to or at the border 161 compared to the storage layer apertures 160c positioned away from the border 161.

The central portion 156 of the storage base layer 132 may be substantially square with each side of the central portion 156 having a length D between about 100 millimeters to about 108 millimeters. In some embodiments, the length D may be between about 106 millimeters to about 108 millimeters. The border 161 of the storage base layer 132 may have a width E between about 4 millimeters to about 11 millimeters and may substantially surround the central portion 156 and the storage layer apertures 160c in the central portion 156. In some embodiments, the width E may be between about 9 millimeters to about 10 millimeters. The periphery 152 of the storage base layer 132 may have a width F between about 25 millimeters to about 35 millimeters and may substantially surround the border 161 and the central portion 156. In some embodiments, the width F may be between about 26 millimeters to about 28 millimeters. Further, the periphery 152 may have a substantially square exterior with each side of the exterior having a length G between about 154 millimeters to about 200 millimeters. In some embodiments, the length G may be between about 176 millimeters to about 184 millimeters. Although FIGS. 4A-4B depict the central portion 156, the border 161, and the periphery 152 of the storage base layer 132 as having a substantially square shape, these and other components of the storage base layer 132 may have any shape to suit a particular application. Further, the dimensions of the storage base layer 132 as described herein may be increased or decreased, for example, substantially in proportion to one another to suit a particular application.

The storage base layer 132 may be a soft, pliable material suitable for providing a fluid seal as described herein. For example, the storage base layer 132 may comprise a silicone gel, a soft silicone, hydrocolloid, hydrogel, polyurethane gel, polyolefin gel, hydrogenated styrenic copolymer gels, a foamed gel, a soft closed cell foam such as polyurethanes and polyolefins that may be coated with an adhesive, polyurethane, polyolefin, and hydrogenated styrenic copolymers, in some embodiments, the storage base layer 132 may have a thickness between about 500 microns (μm) to about 1000 microns (μm). In some embodiments, the storage base layer 132 may have a stiffness between about 5 Shore OO to about 80 Shore OO. Further, the storage base layer 132 may be comprised of hydrophobic or hydrophilic materials.

In some embodiments (not shown), the storage base layer 132 may be a hydrophobic-coated material. For example, the storage base layer 132 may be formed by coating a spaced material, such as, for example, a woven, nonwoven, molded, or extruded mesh with a hydrophobic material. The hydrophobic material for the coating may be a soft silicone, for example. In this manner, the storage layer adhesive 136 may extend through openings in the spaced material analogous to the storage layer apertures 160 as described below.

The storage layer adhesive 136 may be in fluid communication with the storage layer apertures 160 in at least the periphery 152 of the storage base layer 132. In this manner, the storage layer adhesive 136 may be in fluid communication with a portion of the receiving site 26 surrounding the receiving site aperture 38 through the storage layer apertures 160. Analogous to the interface layer adhesive 36 in FIG. 1C, the storage layer adhesive 136 may extend or be pressed through the plurality of storage layer apertures 160 to contact the receiving site 26 for securing the storage dressing 124 to the interface sealing member 24 of the interface dressing 20. The storage layer apertures 160 may provide sufficient contact of the storage layer adhesive 136 to the receiving site 26 to secure the storage dressing 124 about the receiving site aperture 38. However, the configuration of the storage layer apertures 160 and the storage layer adhesive 136, described below, may permit release and repositioning of the storage dressing 124 on the receiving site 26.

Continuing with FIGS. 4A-4B, at least one of the storage layer apertures 160a in the periphery 152 of the storage base layer 132 may be positioned at the edges 159 of the periphery 152 and may have an interior cut open or exposed at the edges 159 that is in fluid communication in a lateral direction with the edges 159. The lateral direction may refer to a direction toward the edges 159 and in the same plane as the storage base layer 132. A plurality of the storage layer apertures 160a in the periphery 152 may be positioned proximate to or at the edges 159 and in fluid communication in a lateral direction with the edges 159. The storage layer apertures 160a positioned proximate to or at the edges 159 may be spaced substantially equidistant around the periphery 152 as shown in FIGS. 4A-4B. However, in some embodiments, the spacing of the storage layer apertures 160a proximate to or at the edges 159 may be irregular. The storage layer adhesive 136 may be in fluid communication with the edges 159 through the storage layer apertures 160a being exposed at the edges 159. In this manner, the storage layer apertures 160a at the edges 159 may permit the storage layer adhesive 136 to flow around the edges 159 for enhancing the adhesion of the edges 159 around the receiving site 26, for example.

The storage layer apertures 160b at the corners 158 of the periphery 152 may be smaller than the storage layer apertures 160a in other portions of the periphery 152 as described above. For a given geometry of the corners 158, the smaller size of the storage layer apertures 160b compared to the storage layer apertures 160a may maximize the surface area of the storage layer adhesive 136 exposed and in fluid communication through the storage layer apertures 160b at the corners 158. For example, as shown in FIGS. 4A-4B, the edges 159 may intersect at substantially a right angle, or about 90 degrees, to define the corners 158. Also as shown, the corners 158 may have a radius of about 10 millimeters. Three of the storage layer apertures 160b having a diameter between about 7.75 millimeters to about 8.75 millimeters may be positioned in a triangular configuration at the corners 158 to maximize the exposed surface area for the storage layer adhesive 136. The size and number of the storage layer apertures 160b in the corners 158 may be adjusted as necessary, depending on the chosen geometry of the corners 158, to maximize the exposed surface area of the storage layer adhesive 136 as described above. Further, the storage layer apertures 160b at the corners 158 may be fully housed within the storage base layer 132, substantially precluding fluid communication in a lateral direction exterior to the corners 158. The storage layer apertures 160b at the corners 158 being fully housed within the storage base layer 132 may substantially preclude fluid communication of the storage layer adhesive 136 exterior to the corners 159, and may provide improved handling of the storage dressing 124 during deployment. Further, the exterior of the corners 158 being substantially free of the storage layer adhesive 136 may increase the flexibility of the corners 158 to enhance comfort.

Similar to the storage layer apertures 160b in the corners 158, any of the storage layer apertures 160 may be adjusted in size and number to maximize the surface area of the storage layer adhesive 136 in fluid communication through the storage layer apertures 160 for a particular application or geometry of the storage base layer 132. For example, in some embodiments (not shown) the storage layer apertures 160b, or apertures of another size, may be positioned in the periphery 152 and at the border 161. Similarly, the storage layer apertures 160b, or apertures of another size, may be positioned as described above in other locations of the storage base layer 132 that may have a complex geometry or shape.

Similar to the interface layer adhesive 36, the storage layer adhesive 136 may be a medically-acceptable adhesive. The storage layer adhesive 136 may also be flowable. For example, the storage layer adhesive 136 may comprise an acrylic adhesive, rubber adhesive, high-tack silicone adhesive, polyurethane, or other adhesive substance. In some embodiments, the storage layer adhesive 136 may be a pressure-sensitive adhesive comprising an acrylic adhesive with coat weight of 15 grams/m$^2$ (gsm) to 70 grams/m$^2$ (gsm). The storage layer adhesive 136 may be a layer having substantially the same shape as the periphery 152 of the storage base layer 132 as shown in FIG. 4A. In some embodiments, the storage layer adhesive 136 may be a continuous or discontinuous layer. Discontinuities in the storage layer adhesive 136 may be provided by apertures (not shown) in the storage layer adhesive 136. The apertures in the storage layer adhesive 136 may be formed after application of the storage layer adhesive 136 or by coating the storage layer adhesive 136 in patterns, for example, on a side of the storage sealing member 140 adapted to face the receiving site 26. Further, the apertures in the storage layer adhesive 136 may be sized to control the amount of the storage layer adhesive 136 extending through the storage layer apertures 160 in the storage base layer 132 to reach the receiving site 26. The apertures in the storage layer adhesive 136 may also be sized to enhance the Moisture Vapor Transfer Rate (MVTR) of the storage dressing 124, described further below.

Factors that may be utilized to control the adhesion strength of the storage dressing 124 may include the diameter and number of the storage apertures 160 in the storage base layer 132, the thickness of the storage base layer 132, the thickness and amount of the storage layer adhesive 136, and the tackiness of the storage layer adhesive 136. An increase in the amount of the storage layer adhesive 136 extending through the storage layer apertures 160 may correspond to an increase in the adhesion strength of the storage dressing 124. A decrease in the thickness of the storage base layer 132 may correspond to an increase in the amount of the storage layer adhesive 136 extending through the storage layer apertures 160. Thus, the diameter and configuration of the storage layer apertures 160, the thickness of the storage base layer 132, and the amount and tackiness of the storage layer adhesive 136 may be varied to provide a desired adhesion strength for the storage dressing 124. For example, the thickness of the storage base layer 132 may be about 200 microns, the storage layer adhesive 136 may have a thickness of about 30 microns and a tackiness of 2000 grams per 25 centimeter wide strip, and the diameter of the storage layer apertures 160a may be about 10 millimeters.

In some embodiments, the tackiness of the storage layer adhesive 136 may vary in different locations of the storage base layer 132. For example, in locations of the storage base layer 132 where the storage layer apertures 160 are comparatively large, such as the storage layer apertures 160a, the storage layer adhesive 136 may have a lower tackiness than other locations of the storage base layer 132 where the storage layer apertures 160 are smaller, such as the storage layer apertures 160b and 160c. In this manner, locations of the storage base layer 132 having larger storage layer apertures 160 and lower tackiness storage layer adhesive 136 may have an adhesion strength comparable to locations having smaller storage layer apertures 160 and higher tackiness storage layer adhesive 136.

Referring to FIG. 4B, a release liner 162 may be attached to or positioned adjacent to the storage base layer 132 to protect the storage layer adhesive 136 prior to application of the storage dressing 124 to the receiving site 26. Prior to application of the storage dressing 124, the storage base layer 132 may be positioned between the storage sealing member 140 and the release liner 162. Removal of the release liner 162 may expose the storage base layer 132 and the storage layer adhesive 136 for application of the storage dressing 124 to the receiving site 26. The release liner 162 may also provide stiffness to assist with deployment of the storage dressing 124.

The release liner 162 may be, for example, a casting paper, a film, or polyethylene. Further, the release liner 162 may be a polyester material such as polyethylene terephthalate (PET), or similar polar semi-crystalline polymer. The use of a polar semi-crystalline polymer for the release liner 162 may substantially preclude wrinkling or other deformation of the storage dressing 124. For example, the polar semi-crystalline polymer may be highly orientated and resistant to softening, swelling, or other deformation that may occur when brought into contact with components of the storage dressing 124, or when subjected to temperature or environmental variations, or sterilization. Further, a release agent may be disposed on a side of the release liner 162 that is configured to contact the storage base layer 132. For example, the release agent may be a silicone coating and may have a release factor suitable to facilitate removal of the release liner 162 by hand and without damaging or deforming the storage dressing 124. In some embodiments, the release agent may be fluorosilicone. In other embodiments, the release liner 162 may be uncoated or otherwise used without a release agent.

Referring to FIGS. 3-4B, the storage sealing member 140 may have a periphery 164 and a central portion 168. The storage sealing member 140 may additionally include an aperture 170, as described below. The periphery 164 of the storage sealing member 140 may be positioned proximate to the periphery 152 of the storage base layer 132 such that the central portion 168 of the storage sealing member 140 and the central portion 156 of the storage base layer 132 define an enclosure 172. The storage layer adhesive 136 may be positioned at least between the periphery 164 of the storage sealing member 140 and the periphery 152 of the storage base layer 132. The storage sealing member 140 may cover the receiving site 26 and the receiving site aperture 38 to provide a fluid seal and a sealed storage space 174 between the receiving site 26 and the storage sealing member 140. The storage base layer 132 may be positioned between the storage sealing member 140 and the receiving site 26 of the interface sealing member 24. The sealed storage space 174 may be in fluid communication with the sealed treatment space 30 through the receiving site aperture 38, for example. Further, the enclosure 172, may provide a portion of the sealed storage space 174 when the storage sealing member 140 is positioned at the receiving site 26 as described.

In some embodiments, a portion of the periphery 164 of the storage sealing member 140 may extend beyond the periphery 152 of the storage base layer 132 and into direct contact with the receiving site 26. In other embodiments, the periphery 164 of the storage sealing member 140, for example, may be positioned in contact with the receiving site 26 to provide the sealed storage space 174 without the storage base layer 132. Thus, the storage layer adhesive 136 may be positioned between at least the periphery 164 of the storage sealing member 140 and the receiving site 26. The storage layer adhesive 136 may be disposed on a surface of the storage sealing member 140 adapted to face the receiving site 26 and the storage base layer 132.

Similar to the interface sealing member 24, the storage sealing member 140 may be formed from any material that allows for a fluid seal. A fluid seal may be a seal adequate to maintain reduced pressure at a desired site, if applicable. The storage sealing member 140 may comprise, for example, one or more of the following materials without limitation: hydrophilic polyurethane; cellulosics; hydrophilic polyamides; polyvinyl alcohol; polyvinyl pyrrolidone; hydrophilic acrylics; hydrophilic silicone elastomers; an INSPIRE 2301 material from Expopack Advanced Coatings of Wrexham, United Kingdom having, for example, an MVTR (inverted cup technique) of 14400 g/m$^2$/24 hours and a thickness of about 30 microns; a thin, uncoated polymer drape; natural rubbers; polyisoprene; styrene butadiene rubber; chloroprene rubber; polybutadiene; nitrite rubber; butyl rubber; ethylene propylene rubber; ethylene propylene diene monomer; chlorosulfonated polyethylene; polysulfide rubber; polyurethane (PU); EVA film; co-polyester; silicones; a silicone drape; a 3M Tegaderm® drape; a polyurethane (PU) drape such as one available from Avery Dennison Corporation of Pasadena, Calif.; polyether block polyamide copolymer (PEBAX), for example, from Arkema, France; Expopack 2327; or other appropriate material.

The storage sealing member 140 may be vapor permeable and liquid impermeable, thereby allowing vapor and inhibiting liquids from exiting the sealed storage space 174 provided by the storage dressing 124. In some embodiments, the storage sealing member 140 may be a flexible, breathable film, membrane, or sheet having a high MVTR of, for example, at least about 300 g/m$^2$ per 24 hours. In other embodiments, a low or no vapor transfer drape might be used. The storage sealing member 140 may comprise a range of medically suitable films having a thickness between about 15 microns (μm) to about 50 microns (μm).

The fluid management assembly 144 may be disposed in the enclosure 172 and may include a first wicking layer 176, a second wicking layer 180, and an absorbent layer 184. The absorbent layer 184 may be positioned in fluid communication between the first wicking layer 176 and the second wicking layer 180. The first wicking layer 176 may have a grain structure (not shown) adapted to wick fluid along a surface of the first wicking layer 176. Similarly, the second wicking layer 180 may have a grain structure (not shown) adapted to wick fluid along a surface of the second wicking layer 180. For example, the first wicking layer 176 and the second wicking layer 180 may wick or otherwise transport fluid in a lateral direction along the surfaces of the first wicking layer 176 and the second wicking layer 180, respectively. The surfaces of the first wicking layer 176 and the second wicking layer 180 may be normal relative to the thickness of each of the first wicking layer 176 and the second wicking layer 180. The wicking of fluid along the first wicking layer 176 and the second wicking layer 180 may enhance the distribution of the fluid over a surface area of the absorbent layer 184 that may increase absorbent efficiency and resist fluid blockages. Fluid blockages may be caused by, for example, fluid pooling in a particular location in the absorbent layer 184 rather than being distributed more uniformly across the absorbent layer 184. The laminate combination of the first wicking layer 176, the second wicking layer 180, and the absorbent layer 184 may be adapted as described above to maintain an open structure, resistant to blockage, capable of maintaining fluid communication with, for example, the interface dressing 20.

Referring to the embodiments of the fluid management assembly 144 depicted in FIGS. 1A, 2A, 3, 5, and 6, a peripheral portion 186 of the first wicking layer 176 may be coupled to a peripheral portion 187 of the second wicking layer 180 to define a wicking layer enclosure 188 between the first wicking layer 176 and the second wicking layer 180. In some exemplary embodiments, the wicking layer enclosure 188 may surround or otherwise encapsulate the absorbent layer 184 between the first wicking layer 176 and the second wicking layer 180.

Figure 5:
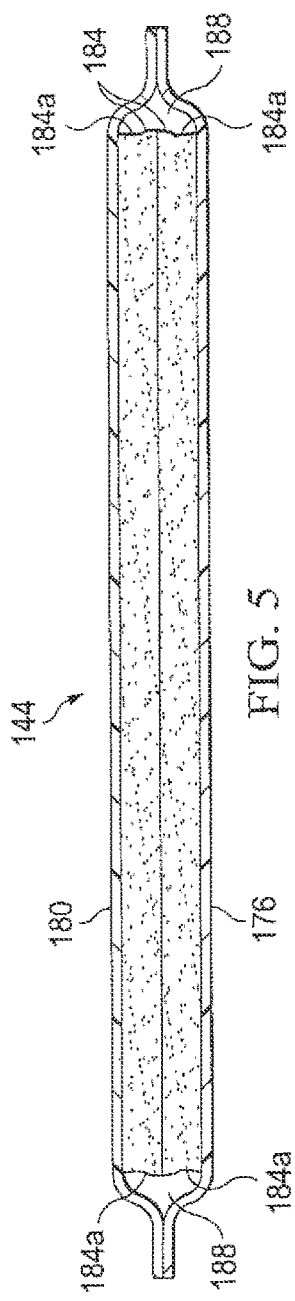
FIG. 5 is a cut-away view of an illustrative embodiment of a fluid management assembly according to the storage dressing of FIG. 3.
Figure 6:
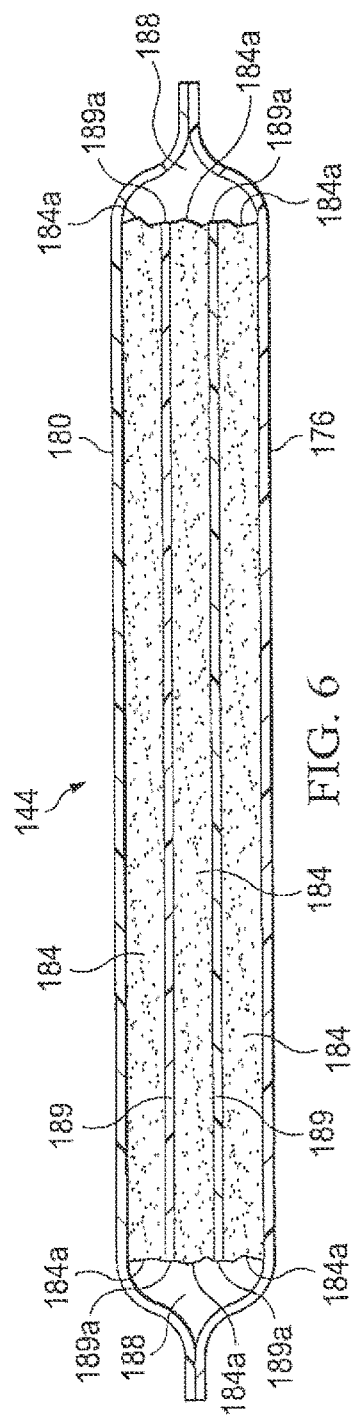
FIG. 6 is a cut-away view of another illustrative embodiment of a fluid management assembly according to the storage dressing of FIG. 3.
Figure 7:
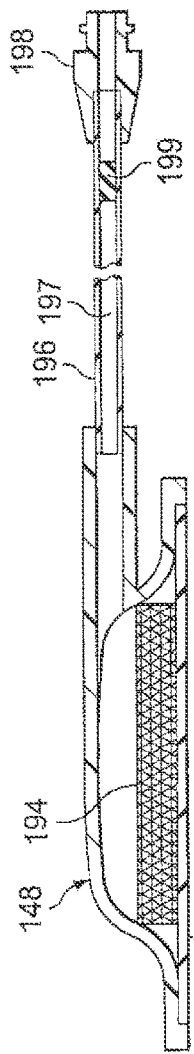
FIG. 7 is a cut-away view of an illustrative embodiment of a conduit interface depicted in the storage dressing of FIG. 3.

Referring to FIGS. 5 and 6, the fluid management assembly 144 may include, without limitation, any number of wicking layers and absorbent layers as desired for treating a particular tissue site. For example, the absorbent layer 184 may be a plurality of absorbent layers 184 positioned in fluid communication between the first wicking layer 176 and the second wicking layer 180 as described above. Further, as depicted in FIG. 6, at least one intermediate wicking layer 189 may be disposed in fluid communication between the plurality of absorbent layers 184. Similar to the absorbent layer 184 described above, the plurality of absorbent layers 184 and the at least one intermediate wicking layer 189 may be positioned within the wicking layer enclosure 188.

In some embodiments, components of the storage dressing 124 may be removed to suit different applications or to reduce material cost. For example, the absorbent layer 184 may be disposed between the storage sealing member 140 and the receiving site 26 with the storage base layer 132, the first wicking layer 176, and the second wicking layer 180 omitted. Thus, the storage sealing member 140 may cover the absorbent layer 184 at the receiving site 26, and the absorbent layer 184 may be sized for positioning in the sealed storage space 174 adjacent to or in direct contact with the receiving site 26. Further, the receiving site aperture 38 may provide fluid communication between the absorbent layer 184 and the interface manifold 22. The non-adherent treatment 40 may be adapted to releaseably or non-permanently secure the storage sealing member 140 to the receiving site 26 as described herein.

In the embodiments of FIGS. 5 and 6, sides 184a of the absorbent layers 184 may remain in fluid communication with one another for enhancing efficiency. Similarly, in the embodiment of FIG. 6, sides 189a of the at least one intermediate wicking layer 189 may remain in fluid communication with one another and with the sides 184a of the absorbent layers 184. Further, including additional absorbent layers 184 may increase the absorbent mass of the fluid management assembly 144 and generally provide greater fluid capacity. However, for a given absorbent mass, multiple light coat-weight absorbent layers 184 may be utilized rather than a single heavy coat-weight absorbent layer 184 to provide a greater absorbent surface area for further enhancing the absorbent efficiency.

In some embodiments, the absorbent layer 184 may be a hydrophilic material adapted to absorb fluid from, for example, the tissue site 12. Materials suitable for the absorbent layer 184 may include Luquafleece® material, Texsus FP2326, BASF 402C, Technical Absorbents 2317 available from Technical Absorbents (www.techabsorbents.com), sodium polyacrylate super absorbers, cellulosics (carboxy methyl cellulose and salts such as sodium CMC), or alginates. Materials suitable for the first wicking layer 176 and the second wicking layer 180 may include any material having a grain structure capable of wicking fluid as described herein, such as, for example, Libeltex TDL2 80 gsm.

The fluid management assembly 144 may be a pre-laminated structure manufactured at a single location or individual layers of material stacked upon one another as described above. Individual layers of the fluid management assembly 144 may be bonded or otherwise secured to one another without adversely affecting fluid management by, for example, utilizing a solvent or non-solvent adhesive, or by thermal welding. Further, the fluid management assembly 144 may be coupled to the border 161 of the base layer 132 in any suitable manner, such as, for example, by a weld or an adhesive. The border 161 being free of the apertures 160 as described above may provide a flexible barrier between the fluid management assembly 144 and the tissue site 104 for enhancing comfort.

In some embodiments, the enclosure 172 defined by the storage base layer 132 and the storage sealing member 140 may include an anti-microbial layer 190. The addition of the anti-microbial layer 190 may reduce the probability of excessive bacterial growth within the storage dressing 124 to permit the storage dressing 124 to remain in place for an extended period. The anti-microbial layer 190 may be, for example, an additional layer included as a part of the fluid management assembly 144 as depicted in FIG. 3, or a coating of an anti-microbial agent disposed in any suitable location within the storage dressing 124. The anti-microbial layer 190 may be comprised of elemental silver or similar compound, for example. In some embodiments, the anti-microbial agent may be formulated in any suitable manner into other components of the storage dressing 124.

Referring to FIGS. 1A, 2A, 3, and 7, the conduit interface 148 may be positioned proximate to the storage sealing member 140 and in fluid communication with the storage dressing 124 through the aperture 170 in the storage sealing member 140 to provide reduced pressure from the reduced-pressure source 128 to the storage dressing 124. Specifically, the conduit interface 148 may be positioned in fluid communication with the enclosure 172, including the absorbent layer 184, of the storage dressing 124. The conduit interface 148 may also be positioned in fluid communication with the interface manifold 22.

The conduit interface 148 may comprise a medical-grade, soft polymer or other pliable material. As non-limiting examples, the conduit interface 148 may be formed from polyurethane, polyethylene, polyvinyl chloride (PVC), fluorosilicone, or ethylene-propylene, etc. in some illustrative, non-limiting embodiments, the conduit interface 148 may be molded from DEHP-free PVC. The conduit interface 148 may be formed in any suitable manner such as by molding, casting, machining, or extruding. Further, the conduit interface 148 may be formed as an integral unit or as individual components and may be coupled to the storage dressing 124 by, for example, adhesive or welding.

In some embodiments, the conduit interface 148 may be formed of an absorbent material having absorbent and evaporative properties. The absorbent material may be vapor permeable and liquid impermeable, thereby being configured to permit vapor to be absorbed into and evaporated from the material through permeation while inhibiting permeation of liquids. The absorbent material may be, for example, a hydrophilic polymer such as a hydrophilic polyurethane. Although the term hydrophilic polymer may be used in the illustrative embodiments that follow, any absorbent material having the properties described herein may be suitable. Further, the absorbent material or hydrophilic polymer may be suitable for use in various components of the system 10 as described herein.

The use of such a hydrophilic polymer for the conduit interface 148 may permit liquids in the conduit interface 148 to evaporate, or otherwise dissipate, during operation. For example, the hydrophilic polymer may allow the liquid to permeate or pass through the conduit interface 148 as vapor, in a gaseous phase, and evaporate into the atmosphere external to the conduit interface 148. Such liquids may be, for example, condensate or other liquids. Condensate may form, for example, as a result of a decrease in temperature within the conduit interface 148, or other components of the system 10, relative to the temperature at the tissue site 12. Removal or dissipation of liquids from the conduit interface 148 may increase visual appeal and prevent odor. Further, such removal of liquids may also increase efficiency and reliability by reducing blockages and other interference with the components of the system 10.

Similar to the conduit interface 148, other components of the system 10 may be formed of an absorbent material or a hydrophilic polymer. The absorptive and evaporative properties of the hydrophilic polymer may also facilitate removal and dissipation of liquids residing in other components of the system 10 by evaporation. Such evaporation may leave behind a substantially solid or gel-like waste. The substantially solid or gel-like waste may be cheaper to dispose than liquids, providing a cost savings for operation of the system 10. The hydrophilic polymer may be used for other components in the system 10 where the management of liquids is beneficial.

In some embodiments, the absorbent material or hydrophilic polymer may have an absorbent capacity in a saturated state that is substantially equivalent to the mass of the hydrophilic polymer in an unsaturated state. The hydrophilic polymer may be fully saturated with vapor in the saturated state and substantially free of vapor in the unsaturated state. In both the saturated state and the unsaturated state, the hydrophilic polymer may retain substantially the same physical, mechanical, and structural properties. For example, the hydrophilic polymer may have a hardness in the unsaturated state that is substantially the same as a hardness of the hydrophilic polymer in the saturated state. The hydrophilic polymer and the components of the system 10 incorporating the hydrophilic polymer may also have a size that is substantially the same in both the unsaturated state and the saturated state. Further, the hydrophilic polymer may remain dry, cool to the touch, and pneumatically sealed in the saturated state and the unsaturated state. The hydrophilic polymer may also remain substantially the same color in the saturated state and the unsaturated state. In this manner, this hydrophilic polymer may retain sufficient strength and other physical properties to remain suitable for use in the system 10. An example of such a hydrophilic polymer is offered under the trade name Techophilic HP-93A-100, available from The Lubrizol Corporation of Wickliffe, Ohio, United States. Techophilic HP-93A-100 is an absorbent hydrophilic thermoplastic polyurethane capable of absorbing 100% of the unsaturated mass of the polyurethane in water and having a durometer or Shore Hardness of about 83 Shore A.

The conduit interface 148 may carry an odor filter 194 adapted to substantially preclude the passage of odors from the tissue site 12 out of the sealed storage space 174. Further, the conduit interface 148 may carry a primary hydrophobic filter 195 adapted to substantially preclude the passage of liquids out of the sealed storage space 174. The odor filter 194 and the primary hydrophobic filter 195 may be disposed in the conduit interface 148, or other suitable location, such that fluid communication between the reduced-pressure source 128 and the storage dressing 124 is provided through the odor filter 194 and the primary hydrophobic filter 195. In some embodiments, the odor filter 194 and the primary hydrophobic filter 195 may be secured within the conduit interface 148 in any suitable manner, such as by adhesive or welding. In other embodiments, the odor filter 194 and the primary hydrophobic filter 195 may be positioned in any exit location in the storage dressing 124 that is in fluid communication with the atmosphere or the reduced-pressure source 128. The odor filter 194 may also be positioned in any suitable location in the system 10 that is in fluid communication with the tissue site 12.

The odor filter 194 may be comprised of a carbon material in the form of a layer or particulate. For example, the odor filter 194 may comprise a woven carbon cloth filter such as those manufactured by Chemviron Carbon, Ltd. of Lancashire, United Kingdom (www.chemvironcarbon.com). The primary hydrophobic filter 195 may be comprised of a material that is liquid impermeable and vapor permeable. For example, the primary hydrophobic filter 195 may comprise a material manufactured under the designation MMT-314 or MMT-332 by W.L. Gore & Associates, Inc. of Newark, Del., United States, or similar materials. The primary hydrophobic filter 195 may be provided in the form of a membrane or layer. Further, in some embodiments, the filter 195 may be an oleophobic filter.

Referring to FIGS. 1A and 2A, the reduced-pressure source 128 may provide reduced pressure as part of the system 10. The reduced-pressure source 128 may be positioned in fluid communication with the interface manifold 22. In some embodiments, the reduce-pressure source 128 may be in fluid communication with the interface manifold 22 through at least the absorbent layer 184. The reduced-pressure source 128 may be any suitable device for providing reduced pressure, such as, for example, a vacuum pump, wall suction, hand pump, or other source.

As used herein, "reduced pressure" may refer to a pressure less than the ambient pressure at a tissue site being subjected to treatment. In some embodiments, the reduced pressure may be less than the atmospheric pressure. The reduced pressure may also be less than a hydrostatic pressure at a tissue site. Unless otherwise indicated, values of pressure stated herein are gauge pressures. While the amount and nature of reduced pressure applied to a tissue site may vary according to the application, in some embodiments, the reduced pressure may be between about −5 mm Hg to about −500 mm Hg. In other embodiments, the reduced pressure may be between about −100 mm Hg to about −200 mm Hg.

The reduced pressure delivered may be constant or varied (patterned or random), and may be delivered continuously or intermittently. Although the terms "vacuum" and "negative pressure" may be used to describe the pressure applied to a tissue site, the actual pressure applied to the tissue site may be more than the pressure normally associated with a complete vacuum. Consistent with the use herein, an increase in reduced pressure or vacuum pressure may refer to a relative reduction in absolute pressure. An increase in reduced pressure may correspond to a reduction in pressure (more negative relative to ambient pressure) and a decrease in reduced pressure may correspond to an increase in pressure (less negative relative to ambient pressure).

As shown in FIGS. 1A, 2A, 3, and 7, a conduit 196 having an internal lumen 197 may be coupled in fluid communication between the reduced-pressure source 128 and the storage dressing 124. The internal lumen 197 may have an internal diameter between about 0.5 millimeters to about 3.0 millimeters. In some embodiments, the internal diameter of the internal lumen 197 may be between about 1 millimeter to about 2 millimeters. The conduit interface 148 may be coupled in fluid communication with the storage dressing 124 and adapted to connect between the conduit 196 and the storage dressing 124 for providing fluid communication with the reduced-pressure source 128. The conduit interface 148 may be fluidly coupled to the conduit 196 in any suitable manner, such as, for example, by an adhesive, solvent or non-solvent bonding, welding, or interference fit. The aperture 170 in the storage sealing member 140 may provide fluid communication between the storage dressing 124 and the conduit interface 148. The conduit interface 148 may be in fluid communication with the enclosure 172 and the sealed storage space 174 through the aperture 170 in the storage sealing member 140. In some embodiments, the conduit 196 may be inserted into the storage dressing 124 through the aperture 170 in the storage sealing member 110 to provide fluid communication with the reduced-pressure source 128 without use of the conduit interface 148. The reduced-pressure source 128 may also be directly coupled in fluid communication with the storage dressing 124 or the storage sealing member 140 without use of the conduit 196. The conduit 196 may be, for example, a flexible polymer tube. A distal end of the conduit 196 may include a coupling 198 for attachment to the reduced-pressure source 128.

The conduit 196 may have a secondary hydrophobic filter 199 disposed in the infernal lumen 197 such that fluid communication between the reduced-pressure source 128 and the storage dressing 124 is provided through the secondary hydrophobic filter 199. The secondary hydrophobic filter 199 may be, for example, a porous, sintered polymer cylinder sized to fit the dimensions of the internal lumen 197 to substantially preclude liquid from bypassing the cylinder. The secondary hydrophobic filter 199 may also be treated with an absorbent material adapted to swell when brought into contact with liquid to block the flow of the liquid. The secondary hydrophobic filter 199 may be positioned at any location within the internal lumen 197. However, positioning the secondary hydrophobic filter 199 within the internal lumen 197 closer toward the reduced-pressure source 128, rather than the storage dressing 124, may allow a user to detect the presence of liquid in the internal lumen 197.

In some embodiments, the conduit 196 and the coupling 198 may be formed of an absorbent material or a hydrophilic polymer as described above for the conduit interface 148. In this manner, the conduit 196 and the coupling 198 may permit liquids in the conduit 196 and the coupling 198 to evaporate, or otherwise dissipate, as described above for the conduit interface 148. The conduit 196 and the coupling 198 may be, for example, molded from the hydrophilic polymer separately, as individual components, or together as an integral component. Further, a wall of the conduit 196 defining the internal lumen 197 may be extruded from the hydrophilic polymer. The conduit 196 may be less than about 1 meter in length, but may have any length to suit a particular application. In some embodiments, a length of about 1 foot or 304.8 millimeters may provide enough absorbent and evaporative surface area to suit many applications, and may provide a cost savings compared to longer lengths. If an application requires additional length for the conduit 196, the absorbent hydrophilic polymer may be coupled in fluid communication with a length of conduit formed of a non-absorbent hydrophobic polymer to provide additional cost savings.

According to an illustrative embodiment of operation of the system 10, the inter ace manifold 22 may be disposed against or proximate to the tissue site 12. The interior facing side 32 of the interface sealing member 24 may be positioned to cover the interface manifold 22 at the tissue site 12 and tissue surrounding the tissue site 12. The interface base layer 28 and/or the interface layer adhesive 36 may be configured and positioned as described above for providing the sealed treatment space 30 between the interface sealing member 24 and the tissue site 12. The receiving site aperture 38 may be cut through the interface sealing member 24, the interface base layer 28, and the interface layer adhesive 36 as applicable and in any suitable manner for providing fluid communication between the receiving site 26 and the interface manifold 22.

The storage dressing 124 may be applied over the receiving site 26 of the interface dressing 20 and about the receiving site aperture 38 to form the sealed storage space 174. In some embodiments, the storage base layer 132 may be applied covering the receiving site aperture 38 and a portion of the receiving site 26 surrounding the receiving site aperture 38. Once the storage dressing 124 is in the desired position, a force may be applied, for example, by hand, on an exterior of the storage sealing member 140. The force applied to the storage sealing member 140 may cause at least some portion of the storage layer adhesive 136 to penetrate or extend through the storage layer apertures 160 and into contact with the receiving site 26 to releaseably adhere the storage dressing 124 about the receiving site 26. In this manner, the configuration of the storage dressing 124 described above may provide a reliable seal against the receiving site 26 while permitting removal and repositioning of the storage dressing 124 on the interface dressing 20 without damaging the interface sealing member 24. Further, the non-adherent treatment 40 at the receiving site 26 may further enhance the ability of a user to reposition or remove the storage dressing 124 for replacement.

As the interface dressing 20 and the storage dressing 124 come into contact with fluid from the tissue site 12, the fluid may move through the storage layer apertures 160 toward the fluid management assembly 144 in the storage dressing 124. The fluid management assembly 144 may wick or otherwise move the fluid through the interface manifold 22 and away from the tissue site 12. As described above, the interface manifold 22 may be adapted to communicate fluid from the tissue site 12 rather than store the fluid. Thus, the fluid management assembly 144 may be more absorbent than the interface manifold 22. The fluid management assembly 144 being more absorbent than the interface manifold 22 may provide an absorbent gradient that may attract fluid from the tissue site 12 or the interface manifold 22 to the fluid management assembly 144. Thus, in some embodiments, the fluid management assembly 144 may be adapted to wick, pull, draw, or otherwise attract fluid from the tissue site 12 through the interface manifold 22. In the fluid management assembly 144, the fluid may initially come into contact with the first wicking layer 176. The first wicking layer 176 may distribute the fluid laterally along the surface of the first wicking layer 176 as described above for absorption and storage within the absorbent layer 184. Similarly, fluid coming into contact with the second wicking layer 180 may be distributed laterally along the surface of the second wicking layer 180 for absorption within the absorbent layer 184.

In some embodiments, a method of treating the tissue site 12 may include positioning the interface dressing 20 on the tissue site 12 and in fluid communication with the tissue site 12. Further, the method may include releaseably securing the storage dressing 124 to the interface dressing 20 in fluid communication with the interface dressing 20, and applying reduced pressure to the storage dressing 124. Further, the method may include extracting fluid from the tissue site 12 through the interface dressing 20, and storing fluid extracted through the interface dressing 20 within the storage dressing 124. The storage dressing 124 may be in fluid communication with the tissue site 12 through the interface dressing 20. In some embodiments, the non-adherent treatment 40 may be positioned between the interface dressing 20 and the storage dressing 124.

In some embodiments, the storage dressing 124 may be a first storage dressing and the method may further include removing the first storage dressing from the interface dressing 20; and replacing the first storage dressing with a second storage dressing. In some embodiments, the second storage dressing may be releaseably secured to the interface dressing 20 in fluid communication with the interface dressing 20 after removing the first storage dressing. In some embodiments, removing the first storage dressing from the interface dressing 20 may occur after the first storage dressing is substantially full of fluid.

In some embodiments, the interface dressing 20 may include an interface manifold 22 and an interface sealing member 24. Positioning the interface dressing 20 on the tissue site 12 may include: positioning the interface manifold 22 on the tissue site 12 in fluid communication with the tissue site 12; and covering the interface manifold 22 and tissue surrounding the tissue site 12 with the interface sealing member 24 to provide a sealed treatment space 30 between the interface sealing member 24 and the tissue site 12.

In some embodiments, the method may include forming an aperture 38 through the interface sealing member 24. The aperture 38 may be adapted to provide fluid communication with the interface manifold 22 through the interface sealing member 24. In some embodiments, forming the aperture 38 through the interface sealing member 24 may occur before releaseably securing the storage dressing 124 to the interface dressing 20.

In some embodiments, the storage dressing 124 may include the absorbent layer 184 and the storage sealing member 140. The method may further include: positioning the absorbent layer 184 on the exterior facing side 34 of the interface dressing 20; and covering the absorbent layer 184 with the storage sealing member 140 to provide the sealed storage space 174 between the storage sealing member 140 and the exterior facing side 34 of the interface dressing 20.

In some embodiments, the storage dressing 124 may include the absorbent layer 184 and the storage sealing member 140. The method may further include: positioning the absorbent layer 184 on the exterior facing side 34 of the interface sealing member 24 in fluid communication with the aperture 38 in the interface sealing member 24; and covering the absorbent layer 184 with the storage sealing member 140 to provide the sealed storage space 174 between the storage sealing member 140 and the exterior facing side 34 of the interface sealing member 24.

Although this specification discloses advantages in the context of certain illustrative, non-limiting embodiments, various changes, substitutions, permutations, and alterations may be made without departing from the scope of the appended claims. Further, any feature described in connection with any one embodiment may also be applicable to any other embodiment.

We claim:

1. A system for treating a tissue site, comprising:
   an interface manifold adapted to be positioned at the tissue site and to provide fluid communication with the tissue site;
   an interface sealing member having an interior facing side and an exterior facing side, the interface sealing member adapted to provide a sealed treatment space between the interior facing side and the tissue site, the interface manifold sized for positioning in the sealed treatment space;
   a receiving site at the exterior facing side of the interface sealing member;
   an absorbent layer for positioning at the receiving site; and
   a storage sealing member adapted to provide a sealed storage space between the storage sealing member and the receiving site, the absorbent layer sized for positioning in the sealed storage space,
   wherein the receiving site comprises a non-adherent treatment configured to permit the storage sealing member to be releaseably secured to the receiving site.

2. The system of claim 1, further comprising a reduced-pressure source for positioning in fluid communication with the interface manifold.

3. The system of claim 2, further comprising a conduit interface positioned proximate to the storage sealing member and in fluid communication with the absorbent layer, the reduced-pressure source for coupling in fluid communication with the conduit interface to provide reduced pressure to the interface manifold through the absorbent layer.

4. The system of claim 1, further comprising a reduced-pressure source for positioning in fluid communication with the interface manifold through at least the absorbent layer.

5. The system of claim 1, wherein the interface manifold comprises a porous material adapted to distribute reduced pressure to the tissue site.

6. The system of claim 1, wherein the interface manifold comprises foam.

7. The system of claim 1, wherein the interface sealing member comprises a liquid impermeable material adapted to cover the tissue site and tissue surrounding the tissue site.

8. The system of claim 1, wherein a portion of the receiving site is adaptable for providing fluid communication between the exterior facing side and the interior facing side of the interface sealing member.

9. The system of claim 1, wherein a portion of the receiving site is adaptable for providing fluid communication between the absorbent layer and the interface manifold.

10. The system of claim 1, wherein a portion of the receiving site is in fluid communication with the interior facing side of the interface sealing member.

11. The system of claim 1, further comprising a receiving site aperture adapted to be disposed through the interface sealing member at the receiving site for providing fluid communication between the exterior facing side and the interior facing side of the interface sealing member.

12. The system of claim 1, wherein the non-adherent treatment comprises a coating of a non-adherent material.

13. The system of claim 1, further comprising a receiving site aperture adapted to be disposed through the interface sealing member at the receiving site for providing fluid communication between the exterior facing side and the interior facing side of the interface sealing member, the non-adherent treatment surrounding the receiving site aperture.

14. The system of claim 1, further comprising an interface base layer for positioning between the interface sealing member and the tissue site.

15. The system of claim 14, wherein the interface base layer comprises a hydrocolloid.

16. The system of claim 14, wherein the interface base layer comprises silicone.

17. The system of claim 14, wherein the interface base layer comprises a plurality of interface layer apertures disposed through opposing sides of the interface base layer.

18. The system of claim 17, wherein at least a portion of the interface base layer is adapted to surround the tissue site, and wherein the interface layer apertures are adapted to be in fluid communication with the interface manifold and tissue surrounding the tissue site.

19. The system of claim 17, further comprising an interface layer adhesive in fluid communication with the interface layer apertures, the interface layer adhesive being positioned between the interface sealing member and the interface base layer, the interface layer adhesive adapted to be in fluid communication with tissue surrounding the tissue site through the interface layer apertures.

20. The system of claim 1, further comprising an interface base layer and an interface layer adhesive positioned on the interior facing side of the interface sealing member.

21. The system of claim 1, further comprising an interface layer adhesive positioned on the interior facing side of the interface sealing member for facing the tissue site.

22. The system of claim 1, further comprising a storage base layer for positioning between the storage sealing member and the interface sealing member.

23. The system of claim 22, wherein the storage base layer comprises a hydrocolloid.

24. The system of claim 22, wherein the storage base layer comprises silicone.

25. The system of claim 22, wherein the storage base layer comprises a plurality of storage layer apertures disposed through opposing sides of the storage base layer.

26. The system of claim 25, wherein the storage layer apertures are adapted to be in fluid communication with the receiving site.

27. The system of claim 25, further comprising a storage layer adhesive in fluid communication with the storage layer apertures, the storage layer adhesive being positioned between the storage sealing member and the storage base layer, the storage layer adhesive being in fluid communication with the receiving site through the storage layer apertures.

28. The system of claim 22, wherein the absorbent layer is positioned between the storage sealing member and the storage base layer.

29. The system of claim 1, further comprising a storage base layer and a storage layer adhesive positioned on a side of the storage sealing member adapted to face the receiving site.

30. The system of claim 1, further comprising a storage layer adhesive positioned on a side of the storage sealing member adapted to face the receiving site.

31. The system of claim 1, further comprising a first wicking layer and a second wicking layer for positioning in the sealed storage space, the absorbent layer being positioned between the first wicking layer and the second wicking layer.

32. The system of claim 31, wherein a peripheral portion of the first wicking layer is coupled to a peripheral portion of the second wicking layer to provide a wicking layer enclosure surrounding the absorbent layer between the first and the second wicking layer.

33. A system for treating a tissue site, comprising:
an interface manifold adapted to be positioned at the tissue site and to provide fluid communication with the tissue site;
an interface sealing member having an interior facing side and an exterior facing side, the interface sealing member adapted to provide a sealed treatment space between the interior facing side and the tissue site, the interface manifold sized for positioning in the sealed treatment space;
an interface base layer for positioning between the interface sealing member and the tissue site, wherein the interface base layer comprises a plurality of interface layer apertures disposed through opposing sides of the interface base layer;
an interface layer adhesive in fluid communication with the interface layer apertures;
a receiving site at the exterior facing side of the interface sealing member;
an absorbent layer for positioning at the receiving site; and
a storage sealing member adapted to provide a sealed storage space between the storage sealing member and the receiving site, the absorbent layer sized for positioning in the sealed storage space.

34. A system for treating a tissue site, comprising:
an interface manifold adapted to be positioned at the tissue site and to provide fluid communication with the tissue site;
an interface sealing member having an interior facing side and an exterior facing side, the interface sealing member adapted to provide a sealed treatment space between the interior facing side and the tissue site, the interface manifold sized for positioning in the sealed treatment space;
a receiving site at the exterior facing side of the interface sealing member;
an absorbent layer for positioning at the receiving site;
a storage sealing member adapted to provide a sealed storage space between the storage sealing member and the receiving site, the absorbent layer sized for positioning in the sealed storage space; and a first wicking layer and a second wicking layer for positioning in the sealed storage space, the absorbent layer being positioned between the first wicking layer and the second wicking layer.

35. The system of claim 34, wherein a peripheral portion of the first wicking layer is coupled to a peripheral portion of the second wicking layer to provide a wicking layer enclosure surrounding the absorbent layer between the first and the second wicking layer.

\* \* \* \* \*